US009556213B2

(12) United States Patent
Vinogradov et al.

(10) Patent No.: US 9,556,213 B2
(45) Date of Patent: Jan. 31, 2017

(54) PHOSPHORESCENT MESO-UNSUBSTITUTED METALLO-TETRABENZOPORPHYRIN PROBE MOLECULES FOR MEASURING OXYGEN AND IMAGING METHODS

(71) Applicants: Sergei A. Vinogradov, Wynnewood, PA (US); David F. Wilson, Philadelphia, PA (US)

(72) Inventors: Sergei A. Vinogradov, Wynnewood, PA (US); David F. Wilson, Philadelphia, PA (US)

( * ) Notice: Subject to any disclaimer, the term of this patent is extended or adjusted under 35 U.S.C. 154(b) by 353 days.

(21) Appl. No.: 13/778,777

(22) Filed: Feb. 27, 2013

(65) Prior Publication Data
US 2013/0224874 A1    Aug. 29, 2013

Related U.S. Application Data

(60) Provisional application No. 61/603,668, filed on Feb. 27, 2012.

(51) Int. Cl.
| | | |
|---|---|---|
| G01N 21/64 | (2006.01) | |
| C07F 15/00 | (2006.01) | |

(Continued)

(52) U.S. Cl.
CPC ......... *C07F 15/0066* (2013.01); *C07D 257/02* (2013.01); *C07D 275/00* (2013.01);
(Continued)

(58) Field of Classification Search
CPC ...................................... G01N 21/64
(Continued)

(56) References Cited

U.S. PATENT DOCUMENTS

| | | | |
|---|---|---|---|
| 4,568,737 A | 2/1986 | Tomalia | |
| 4,659,676 A * | 4/1987 | Rhyne, Jr. | 436/56 |

(Continued)

OTHER PUBLICATIONS

Stevelmans, S. et al, Journal of the American Chemical Society 1996, 118, 7398-7399.*

(Continued)

*Primary Examiner* — Arlen Soderquist
(74) *Attorney, Agent, or Firm* — Montgomery, McCracken, Walker & Rhoads, LLP; James L. Gannon, II

(57) ABSTRACT

Oxygen levels in biological tissue or systems can be measured by the phosphorescence quenching method using phosphorescent porphyrin probes, also referred to as a dendritic oxygen probes, with controllable quenching parameters and defined biodistributions. Provided are a "next generation" of oxygen sensors with substantially improved phosphorescence emission for better imaging capabilities, ease of use, increasing the quantum efficiency (phosphorescence intensity) and extending their range of applicability including constructing a class of oxygen sensors for making measurements in organic media. In addition, provided are methods for synthesizing new porphyrin constructs in which the porphyrin is made less flexible and more planar, changing with decrease internal quenching, and thereby increasing the phosphorescence emission used for oxygen sensing. Additional methods are provided for structurally modifying the dendrimer used to encapsulate the porphyrin phosphor to provide internal quenching of singlet oxygen molecules formed during oxygen measurements.

11 Claims, 7 Drawing Sheets

KOtBu - potassium tert-butoxide
mCPBA - meta-chloroperbenzooic acid

(51) Int. Cl.
  *C07D 275/00* (2006.01)
  *C07D 257/02* (2006.01)
  *C07D 487/22* (2006.01)
(52) U.S. Cl.
  CPC ......... *C07D 487/22* (2013.01); *G01N 21/643* (2013.01); *Y10T 436/207497* (2015.01)
(58) Field of Classification Search
  USPC .................................. 436/136, 172; 548/402
  See application file for complete search history.

(56) References Cited

U.S. PATENT DOCUMENTS

| | | | |
|---|---|---|---|
| 4,947,850 A | 8/1990 | Vanderkooi | |
| 5,041,516 A | 8/1991 | Frechet | |
| 5,098,475 A | 3/1992 | Winnik | |
| 5,256,193 A | 10/1993 | Winnik | |
| 5,393,795 A | 2/1995 | Hedstrand | |
| 5,393,797 A | 2/1995 | Hedstrand | |
| 5,418,301 A | 5/1995 | Hult | |
| 5,837,865 A | 11/1998 | Vinogradov | |
| 5,912,257 A * | 6/1999 | Prasad et al. | 514/356 |
| 6,165,741 A * | 12/2000 | Wilson et al. | 435/34 |
| 6,362,175 B1* | 3/2002 | Vinogradov et al. | 514/185 |
| 6,413,656 B1* | 7/2002 | Thompson et al. | 428/690 |
| 7,537,842 B2* | 5/2009 | Burn et al. | 313/504 |
| 7,592,074 B2* | 9/2009 | Burn et al. | 428/690 |
| 7,598,381 B2* | 10/2009 | Thompson et al. | 428/690 |
| 2003/0203888 A1 | 10/2003 | Boyle et al. | 514/185 |
| 2005/0042623 A1* | 2/2005 | Ault-Riche et al. | 435/6 |
| 2008/0061681 A1* | 3/2008 | Thompson et al. | 313/504 |
| 2009/0216097 A1* | 8/2009 | Wilson et al. | 600/327 |
| 2011/0014125 A1* | 1/2011 | Bossmann et al. | 424/9.1 |
| 2011/0117020 A1* | 5/2011 | Vinogradov et al. | 424/9.1 |
| 2012/0157824 A1* | 6/2012 | Bossmann et al. | 600/420 |
| 2012/0302743 A1* | 11/2012 | Vail et al. | 540/145 |
| 2012/0308485 A1* | 12/2012 | Ramaiah et al. | 424/9.61 |

OTHER PUBLICATIONS

Collman, J. P. et al, Chemical Communications 1997, 193-194.*
Gorman, C. B. et al, Accounts of Chemical Research 2001, 34, 60-71.*
Rozhkov, V. et al, Macromolecules 2002, 35, 1991-1993 with available supplementary information.*
Vinogradov S. A. et al, SPIE 2002, 4626, 193-200.*
Nishiyama, N. et al, Bioconjugate Chemistry 2003, 14, 58-66.*
Finikova, O. et al, Journal of the American Chemical Society 2003, 125, 4882-4893.*
Ng, D. K. P., C. R. Chimie 2003, 6, 903-910.*
Vestberg, R. et al, Chemistry of Materials 2004, 16, 2794-2804.*
Newkome, G. R. et al, Macromolecules 2004, 37, 8262-8268.*
Ziemer, L. S. et al, Journal of Applied Physiology 2005, 98, 1503-1510.*
Oar, M. A. et al, Chemistry of Materials 2005, 17, 2267-2275.*
Finikova, O. S. et al, Journal of Organic Chemistry 2005, 70, 9562-9572 with available supplementary material.*
Jang, W.-D. et al, Journal of Controlled Release 2006, 113, 75-79.*
Finikova, O. S. et al, Journal of Physical Chemistry A 2007, 111, 6977-6990 with available supplementary material.*
Finikova, O. S. et al, Journal of Photochemistry and Photobiology A: Chemistry 2008, 198, 75-84.*
Filatov, M. A. et al, Journal of Organic Chemistry 2008, 73, 4175-4185 with available supplementary material.*
Lebedev, A. Y. et al, Journal of Physical Chemistry A 2008, 112, 7723-7733 with available supplementary material.*
Lebedev, A. Y. et al, Applied Chemistry of Materials & Interfaces 2009, 1, 1292-1304 with available supplementary material.*
Sinks, L. E. et al, OSA/DH/FTS/HISE/NTM/OTA 2009, 3 pages.*
Sinks, L. E. et al, Journal of Physical Chemistry B 2010, 114, 14373-14382 with available supplementary material.*

Parpaleix et al., "Imaging local neuronal activity by monitoring PO2, transients in capillaries" Nature Medicine 19:241-246 (2013).
Piert et al.,"Hypoxia-Specific Tumor Imaging with 18F-Fluoroazomycin Arabinoside," Nucl. Med. 46:106-113 (2005).
Rajendran et al., "Imaging hypoxia and angiogenesis in tumors," Radiol. Clin. North Am. 43:169-187 (2005).
Rietveld et al., "Dendrimers with tetrabenzoporphyrin cores: near infrared phosphors for in vivo oxygen imaging," Tetrahedron 59:3821 (2003).
Rumsey et al., "Oxygen tension imaging in the mouse retina," Science. 241:1649-1652 (1988).
Sakadzicet al., "Two-photon high-resolution measurement of partial pressure of oxygen in cerebral vasculature and tissue," Nat. Methods 7,755-U125 (2010).
Senge "Nucleophilic Substitution as a Tool for the Synthesis of Unsymmetrical Porphyrins," Accounts of Chemical Research 38: 733-743 (2005).
Subramanian et al., "Radio frequency continuous-wave and time-domain EPR imaging and Overhauser-enhanced magnetic resonance imaging of small animals: instrumental developments and comparison of relative merits for functional imaging," NMR Biomed. 17:263-294 (2004).
Tripathy et al., "Photophysics of Soret-Excited Tetrapyrroles in Solution. IV. Radiationless Decay and Triplet—Triplet Annihilation Investigated Using Tetraphenylporphinato Sn(IV)," J. Phys. Chem. A 112:5824 (2008).
Vanderkooi et al., "An Optical Method for Measurement of Dioxygen Concentration Based upon Quenching of Phosphorescence", J. Biol. Chem. 262, No. 12:5476-5482 (1987).
Vicente et al., "Synthesis and Cycloaddition Reactions of Pyrrole-Fused 3-Sulfolenes: a New Versatile Route to Tetrabenzoporphyrins," Tetrahedron Letters 38:3639-3642 (1997).
Vinogradov et al., "Tetrabenzporphyrins: new phosphorescent probes for oxygen measurement" J. Chem. Soc. Perkin Trans. II, 2, 103-111 (1995).
Vinogradov et al., "Non-invasive imaging of the distribution of oxygen in tissue in vivo using near infra-red phosphors," Biophys. J. 70, 1609-1617 (1996).
Vinogradov et al., "Dendritic polyglutamic porphyrins: probing porphyrin protection by oxygen dependent quenching of phosphorescence" Chem. Europ. J., 5 (4), 1388-1347 (1999).
Vinogradov et al., "Recursive Maximum Entropy Algorithm and its Application to Luminescence Lifetime Distribution Recovery" Applied Spectroscopy, 54:849 (2000).
Vinogradov "Arylamide dendrimers with flexible linkers via haloacyl halide method" Organic Letters 7: 1761-1764 (2005).
Vinogradov et al, "Porphyrin-dendrimers as biological oxygen sensors," In Designing Dendrimers (Capagna, Ceroni, Eds.), Wiley, New York (2012), 463-502.
Ibaraki et al., "Inter-individual variations of CBF and oxygen consumption in relation to hemoglobin concentration: a PET study," J. Cerebral Blood Flow and Metabolism 29:S381—S393 (2009).
Yaseen et al., "Optical monitoring of oxygen tension in cortical microvessels with confocal microscopy," Opt Express. 17:22341-22350 (2009).
Zhang et al., "Čerenkov radiation emission and excited luminescence (CREL) sensitivity during external beam radiation therapy: Monte Carlo and tissue oxygenation phantom studies," Biomedical Optics Express 3:2381 (2012).
Apisarnthanarax et al., "Current Imaging Paradigms in Radiation Oncology," Radiat. Res. 163, 1-25 (2005).
Apreleva et al., "Feasibility of diffuse optical imaging with long-lived luminescent probes," Optic Letters; 31 (8):1082-4 (2006).
Apreleva et al., "Influence of optical heterogeneities on reconstruction of spatial phosphorescence lifetime distributions," Optics Letters. 33,782-784 (2008).
Ballinger, "Imaging hypoxia in tumors," Sem. Nucl. Med. 31:321-329 (2001).
Barton, "A new synthesis of pyrroles from nitroalkenes," J. Chem. Soc. 1098 (1985).
Barton et al., "A useful synthesis of pyrroles from nitroolefins," Tetrahedron, vol. 46, 7587-7598 (1990).

(56) References Cited

OTHER PUBLICATIONS

Berkowitz et al., "Correction of Early Subnormal Superior Hemiretinal ΔPO2 Predicts Therapeutic Efficacy in Experimental Diabetic Retinopathy," Invest. Ophthalmol. Visual Sci. 40:2100-2105 (1999).
Brinas, "Phosphorescent Oxygen Sensor with Dendritic Protection and Two-Photon Absorbing Antenna,". J. Am. Chem. Soc.; 127:11851-11862 (2005).
Brunel et al., "Fetal Brain Injury," J. Neuroradiology 31:123-137 (2004).
Caliceti et al., "Pharmacokinetic and biodistribution properties of poly(ethylene glycol)-protein conjugates," Advanced Drug Delivery Reviews 55:1261-1277 (2003).
Ceroni et al., "Evaluation of phototoxicity of dendritic porphyrin-based phosphorescent oxygen probes: an in vitro study," Photochem. Photobiol. Sci. 10:1056-1065 (2011).
Cheprakov et al., "The dihydroisoindole approach to linearly annelated-extended porphyrinsJ. Porphyrins and Phthalocyanines," 13:291-303 (2009).
Dandliker et al., "Dendritic Porphyrins: Modulating REdox Potentials of Electroactive Chromophores with Pendant Multifunctionality," Angewandte Chemie-International (Edition in English) 33:1739 (1994).
Dandliker et al., "Water-Soluble Dendritic Iron Porphyrins: Synthetic Models of Globular Heme Proteins," Angewandte Chemie-International (Edition in English) 34:2725 (1996).
Devor et al., "'Overshoot' of O2 Is Required to Maintain Baseline Tissue Oxygenation at Locations Distal to Blood Vessels," J. Neuroscience 31:13676 (2011).
Dunphy et al., "Oxyphor R2 and G2: phosprs for measuring oxygen by oxygen-dependent quenching of phosphorescence", Anal. Biochem. 310: 191-198 (2002).
Eastwood et al., "Porphyrins: XVIII. Luminescence of (Co), (Ni), Pd, Pt complexes," J. Molecular Spectroscopy 35:359 (1970).
Edwards et al., "Synthesis and Vapor Spectrum of Zinc Tetrabenzporphine," J. Amer. Chem. Soc. 98:7638 (1976).
Esipova et al., "Two new "protected" oxyphors for biological oximetry: properties and application in tumor imaging," Analytical Chem. 83:8756 (2011).
Estrada et al., "Microvascular oxygen quantification using two-photon microscopy," Optics Letters 33:1038 (2008).
Evans et al., "Homeostatic responses to caloric restriction: influence of background metabolic rate" J. Appl. Physiol. 98:1503-1510 (2005).
Fenton et al., "Quantification of tumour vasculature and hypoxia by immunohistochemical staining and HbO2 saturation measurements." Brit. J. Cancer 79:464-471 (1999).
Filatov et al., A Facile and Reliable Method for the Synthesis of Tetrabenzoporphyrin from 4,7-Dihydroisoindole, Europe. J. Org. Chem. 3468 (2007).
Filatov et al., "Synthesis of 5,15-diaryltetrabenzoporphyrins," J. Org. Chem. 73:4175-4185. (2008).
Finikova et al., "An expedient synthesis of substituted tetraaryltetrabenzoporphyrins," Chem. Commun. 261 (2001).
Finikova et al., "Novel route to functionalized tetraaryltetra[2,3]naphthaloporphyrins via oxidative aromatization," J. Org. Chem. 68:7517-7520 (2003).
Finikova et al., "Novel versatile synthesis of substituted tetrabenzoporphyrins," J. Org. Chem. 69:522 (2004).
Finikova et al., "Synthesis and luminescence of soluble meso-unsubstituted tetrabenzo- and tetranaphtho [2,3] porphyrins," J. Org. Chem. 70:9562 (2005).
Finikova et al., "Energy and Electron Transfer in Enhanced Two-Photon-Absorbing Systems with Triplet Cores," J. Physical Chem. A 111:6977-6990 (2007).
Finikova et al., "Oxygen Microscopy by Two-Photon-Excited Phosphorescence," Chem. Phys. Chem. 9:1673-1679 (2008).
Foo et al., "Functional imaging of intratumoral hypoxia," Mol. Imag. Biol. 6:291-305 (2004).
Golub et al., "Microvascular oxygen tension in the rat mesentery," Am. J. Physiol.-Heart and Circulatory Physiol. 294 (1):H21 (2008).
Gorman et al., "Iron-Sulfur Core Dendrimers Display Dramatically Different Electrochemical Behaviors in Films Compared to Solution," J. Am. Chem. Soc., 122(38), 9342-9343 (2000).
Hawker et al., "Unimolecular Micelles and Globular Amphiphiles: Dendritic Macromolecules as Novel Recyclable Solubilization Agents," J. Chem. Soc. Perkin Trans. I 1287 (1993).
Ichimura et al., "Reinvestigation of synthetic methods for zinc meso-tetraphenyltetrabenzoporphyrin," Inorganica Chimica Acta 176:31 (1990).
Ito et al., "A new synthesis of benzoporphyrins using 4,7-dihydro-4,7-ethano-2H-isoindole as a synthon of isoindole," Chemical Communications 1661 (1998).
Ito et al., Chem. Comm. 893 (2000).
Lebedev et al., "Dendritic Phosphorescent Probes for Oxygen Imaging in Biological Systems," ACS Applied Materials & Interfaces 1:1292 (2009).
Lebedev et al., "Effects of Structural Deformations on Optical Properties of Tetrabenzoporphyrins: Free-Bases and Pd Complexes," J. Physical Chem. A, 112:7723-77336 (2008).
Lecoq et al., "Simultaneous two-photon imaging of oxygen and bloodflow in deep cerebral vessels," Nature Medicine 17:893 (2011).
Lee et al., "NIR luminescent oxygen nanosensors with nanoparticle matrix tailored sensitivity," Anal. Chem. 82:8446-8455 (2010).
Newkome et al., "Syntheses of Amine Building Blocks for Dendritic Macromolecule Construction," Synlett 53 (1992).

* cited by examiner

R = alkyl, aryl

PHOSPHORESCENT MESO-UNSUBSTITUTED METALLO-TETRABENZOPORPHYRIN PROBE MOLECULES FOR MEASURING OXYGEN AND IMAGING METHODS

CROSS-REFERENCE TO RELATED APPLICATIONS

The present invention claims priority to U.S. Provisional Application Ser. No. 61/603,668, filed on Feb. 27, 2012, which is incorporated herein in its entirety.

GOVERNMENT INTEREST

This invention was supported in part by funds from the U.S. Government (National Institutes of Health) Grant No. HL0812273, R01EB007279 and the U.S. Government may therefore have certain rights in the invention.

FIELD OF THE INVENTION

The present invention relates to highly accurate and versatile optical method for oxygen measurement, particularly useful for applications in living human and animal tissue, and more particularly to novel phosphorescent probe molecules that possess brighter signal, well-defined chemical composition, and can potentially be used in clinics.

BACKGROUND OF THE INVENTION

The reliable and accurate measurement of oxygen supply in mammalian tissue is important to ensure that the oxygen supply is adequate. The circulatory system employs specialized oxygen-carrying protein molecules in red blood cells to deliver oxygen from the lungs throughout the body. Once dissociated from hemoglobin, oxygen is delivered to its consumption sites in cells by diffusion. It is the measurement of this dissolved unbound oxygen that is most critical for quantifying tissue physiological status. The phosphorescence quenching method underpinning this patent application is unique in its ability to accomplish such a measurement. This method is based on use of special phosphorescent probe molecules, which report on oxygen concentration in the environment with high specificity and accuracy.

Measurements of oxygen by phosphorescence quenching using phosphorescent probes not only provide measurement of oxygen consumption by the tissue, but also allow evaluation of tissue diseased states. Oxygen is a key metabolite, and tissue hypoxia is a critical parameter with respect to various tissue pathologies, such as retinal diseases (Berkowitz et al., *Invest. Ophthalmol. Visual Sci.* 40:2100-2105 (1999); Linsenmeier et al., *Ophthalmol. Visual Sci.* 39:1647-1657 (1998)), brain abnormalities (Vannucci et al., *J. Exp. Biol.* 207:3149-3154 (2004); Brunel et al., *J. Neuroradiology* 31:123-137 (2004); Johnston et al., *Neuroscientist* 8:212-220 (2002)), and cancer (Evans et al., *J. Appl. Physiol.* 98:1503-1510 (2005)). Differing oxygen levels in tissues can be indicative of tissue structure abnormalities, defects, whether caused externally, or by genetic manifestations, resulting from disease.

Imaging tissue oxygen in vivo presents a challenging and important problem. Nevertheless, currently developing imaging technologies for mapping tissue oxygenation (Rajendran et al., *Radiol. Clin. North Am.* 43:169-187 (2005)) (e.g., NMR/EPR (Subramanian et al. *NMR Biomed.* 17:263-294 (2004)), PET (Piert et al., *Nucl. Med.* 46:106-113 (2005); Apisarnthanarax et al., *Rad. Res.* 163:1-25 (2005)), near infrared tomographic techniques (Fenton et al., *Brit. J. Cancer* 79:464-471 (1999); Liu et al., *Appl. Opt.* 39:5231-5243 (2000)), etc (Ballinger, *Sem. Nucl. Med.* 31:321-329 (2001); Foo et al., *Mol. Imag. Biol.* 6:291-305 (2004)) suffer from many deficiencies, including invasiveness, low spatial and/or temporal resolution, lack of absolute calibration, poor specificity, etc., and remain yet to be adequately developed.

The phosphorescence quenching method (Vanderkooi et al., *J. Biol. Chem.* 262:5476-5483 (1987); Wilson & Vinogradov, In: *Handbook of Biomedical Fluorescence.* Mycek M-A, Pogue B W, eds. Marcel Dekker; New York: 2003. Ch. 17) is superior in its ability to directly detect oxygen in tissue. A detailed summary is presented by Vinogradov & Wilson (2012) "Porphyrin-dendrimers as biological oxygen sensors," In *Designing Dendrimers* (Capagna, Ceroni, Eds.), Wiley, New York) following the effective filing date of this invention. When a phosphorescent probe is dissolved in the blood and excited using appropriate illumination, its phosphorescence lifetime and intensity become robust indicators of oxygen concentration in the environment. Phosphorescence quenching is exquisitely sensitive and selective to oxygen, possesses excellent temporal resolution and can be implemented for high-resolution hypoxia imaging in 2D (Rumsey et al., *Science.* 241:1649-1652 (1988); Vinogradov et al., *Biophys. J.* 70:1609-1617 (1996); Shonat et al., *Annal. Biomed. Eng.* 31:1084-1096 (2003)).

Efforts to develop 3D near infrared tomographic modality, include Soloviev et al., *Applied Optics* 42:113 (2003); Soloviev et al., *Applied Optics* 43:564 (2004); Apreleva et al., *Optics Letters* 31:1082 (2006); Apreleva et al., *Applied Optics* 45:8547 (2006); Apreleva et al., *Optics Letters* 33:782 (2008), and recent clinically relevant developments of Cerenkov radiation-induced phosphorescence (Zhang et al., *Biomedical Optics Express* 3:2381 (2012). But highly accurate and versatile methods for measuring oxygen remain to be further developed.

For phosphorescent compounds to be suitable for use as a phosphorescent oxygen probe (aka "phosphor" or "oxyphor") in determination of tissue oxygenation, it is desirable that the compounds have (1) high absorbance in the near infrared region of the spectrum where natural chromophores of tissue, such as hemoglobin or myoglobin, have only very weak absorption; (2) phosphorescence with high quantum yields at room temperature, preferably greater than 0.02; and (3) suitable lifetimes, preferably from about 0.1 to about 1 msec.

A new class of phosphors suitable for oxygen measurement was previously reported in Vinogradov and Wilson, *J. Chem. Soc., Perkin Trans.* 2, 103-111 (1995), and in U.S. Pat. No. 4,947,850, "Method and Apparatus for Imaging an Internal Body Portion of a Host Animal," by Vanderkooi and Wilson), and U.S. Pat. No. 5,837,865, "Phosphorescent Dendritic Macromolecular Compounds for Imaging Tissue Oxygen," by Vinogradov and Wilson), which are incorporated herein by reference. In the general, the phosphorescent probes for oxygen measurements comprise three functional parts: 1) phosphorescent core; 2) encapsulating and protecting ligands and 3) the hydrophilic outer layer, which is usually made of monomethyloligoethyleneglycol or simply polyethyleneglycol (PEG) residues. Parts 2 and 3 comprise the so-called immediate "surrounding environment" of the phosphorescent chromophore.

The functions of the three parts are as follows: a) phosphorescent core provides optical signal (phosphorescence), inducible by red/near infrared excitation sources and responsive to changes in the partial pressure of oxygen (pO$_2$); b) encapsulating ligands allow tuning of the core accessibility to oxygen to optimize probe's sensitivity in the physiological pO$_2$ range; and c) outer layer provides solubility and isolates the probe from interactions with endogenous biological species (proteins, nucleic acids, membranes etc) in order to maintain the calibration constants for quantitative pO$_2$ measurements in biological environments.

Both aforementioned patents teach compounds based on complexes of metals, such as Pd and Pt, with porphyrins and aromatically πt-extended porphyrins, such as, for example, tetrabenzoporphyrin, tetranaphthaloporphyrin, tetraanthraporphrin and various derivatives thereof, which play the role of phosphorescent cores (part 1). These complexes possess bright room temperature phosphorescence, and Pd and Pt complexes of tetrabenzoporphyrins and tetranaphthaloporphyrins are especially desirable because they show strong light absorption in the near IR region (610-650 nm and 700-720 nm, respectively), where tissue is practically transparent. Moreover, Pd tetrabenzoporphyrins (PdTBP) and their derivatives have been shown to have long-lived phosphorescence (~250 μsec) with quantum yields of 0.08-0.10%. These values have been later re-measured against improved fluorescence standards used throughout the remainder of this spefication, and shown to be 0.0015-0.04 (see Esipova et al, *Anal. Chem.* 83:8756 (published on-line Oct. 11, 2011).

Generally, the surrounding environment determines properties of the phosphorescent probe with respect to oxygen measurement, including water solubility, toxicity, oxygen quenching constant, sensitivity of the measurements to chemically active components of tissue, and ease of excretion of the probe from the body through the kidney. It is also desirable to design the surrounding environment, such that it comprises an inert globular structure around the phosphor, through which only small uncharged molecules, i.e., oxygen, can diffuse into the close vicinity of the phosphorescent core for efficient quenching.

The '865 patent above teaches that the optimal surrounding environment for the phosphorescent core is made of dendrons as encapsulating ligands (part 2) and polyethyleneglycols (or oligoethyleneglycols) as the outer layer of the probe (part 3). (Note that together the encapsulating dendrons are said to comprise a dendrimer. Accordingly, the corresponding phosphorescent probes are termed dendritic.) Dendritic probes so far have shown to be superior phosphors for oxygen measurements in biological systems. Many laboratories around the world currently use these molecules for oxygen measurements in the blood, tissue interstitial space, various organs and with application of different modes of the phosphorescence quenching method (see above). See, e.g., Sakadzic et al., *Nat. Methods* 7:755 (2010); Devor et al., *J. Neuroscience* 31:13676 (2011); Lecoq et a, *Nature Medicine* 17:893 (2011); and since the effective filing date of this application, Parpaleix et al., *Nature Medicine* 19:241-246 (2013), which have capitalized on the use of the dendritic oxygen probes to decipher brain energy metabolism in the field of neuroscience. Thus the prior and present art have clearly established tremendous value of dendritic oxygen probes, warranting their further improvement and optimization.

It has therefore been an ongoing need in the art to further improve on the structure of dendritic phosphorescent probes by altering and improving their chemical structure, thereby providing a "next generation" of oxygen sensors with substantially improved phosphorescence emission for better imaging capabilities, ease of use, and range of applicability.

In addition, some of the new molecules in this disclosure provide measurements of oxygen, not only in an aqueous environment, but also in liquid organic media, such as organic solvents and/or oils.

SUMMARY OF THE INVENTION

The present invention provides phosphors comprising a new class of porphyrin-based oxyphors, wherein the porphyrin is made less flexible and more planar, two modifications that the inventors have shown significantly (5-10 fold) increases the quantum yield over the prior art probes, and therefore serve as the bases for significantly improved oxygen sensors. These structurally improved, extended porphyrins are then complexed with dendrimers to surround the phosphorescent core by supramolecular structures which are designed to be highly soluble in either water based media or in liquid organic media, such as organic solvents and/or oils. They provide additional sought-after characteristics of phosphorescent probes such as long-lived phosphorescence and high quantum yields.

In Oxyphors R4 and G4 and in all prior art in the inventor's laboratories the porphyrin probes have all been meso-tetra-aryl substituted porphyrins (having four aryl rings radiating out of the metalloporphyrin structure), which by example have had Pt or Pd cores. To these rings, dendrons are attached forming the dendrimer. By comparison, it is an object of the present invention to provide di-aryl porphyrins, wherein the porphyrin structure is unique in that the construct has only two aryl rings, which are always opposite to one another (e.g., 5,15-diaryl substituted tetrabenzoporphyrins (TBPs)) or have no meso-aryl rings at all (e.g., Pd meso-unsubstituted porphyrins). This change in the porphyrin structure produces a significant (5-10 fold) increase in the phosphorescence quantum yield (0.2-0.4 higher at zero oxygen) and extends triplet state lifetimes (to 60-700 μs) to provide higher oxygen sensitivity than previous models. Structures having fewer aryls would seem to have been easier to synthesize, but that is a deceptive assumption since building tetraarylporphyrins is significantly easier. But the formulation and use of di-arylporphyrins and meso-unsubstituted porphyrins result in significantly improved oxygen sensors.

It is a second object of the invention to provide an improved process for attaching dendrons to the porphyrin. The method appears simple, but in fact, it has not been done before. The improved process first attaches "extension arms" (meaning e.g., aminobutyrate linkers) to the aryl rings on the porphyrins, and then dendrons are attached to the ends of the attached extension arms. In the prior art, the groups to which dendrons are attached on the aryl rings of the porphyrin directly are positioned too close to each other, as a result, bulky dendrons interfere with each other and the whole linking reaction becomes inefficient. However, when extension arms are attached before the dendrons are added, the points of dendron attachment are sufficiently separated in space, and thus facilitate the linking reaction.

It is a third object of the invention to increase excitation cross-sections of the probe using intramolecular Förster-type resonance energy transfer (FRET) by the use of antenna chromophores in the porphyrin-dendrimer structure. The antenna chromophores capture excitation photons, and transfer the energy to the porphyrin by way of FRET. The remaining fluorescent signal, well separated spectrally from the phosphorescence is available for ratiometric oxygen detection, enabling the use of several available laser bands, and effectively making the probes at least 5×, to at least 7×, to as much as 10× brighter without increasing the probes' phototoxicity.

It is a fourth object of the invention to provide dendritic phosphorescent probes suitable for oxygen measurements in selectable either aqueous or liquid organic media, e.g., oils, saturated hydrocarbons, aromatic mineral oils, and the like. By adding a three dimensional supramolecular hydrophobic outer layer to the termini of the dendrimers, the entire molecule remains folded, but becomes in highly soluble in certain organic solvents, thus for the first time enabling oxygen measurements in such organic solvents.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

in FIG. 5B the Jablonski diagram, and in FIG. 5C the corresponding spectra.

DETAILED DESCRIPTION OF CERTAIN EMBODIMENTS OF THE INVENTION

Figure 1:
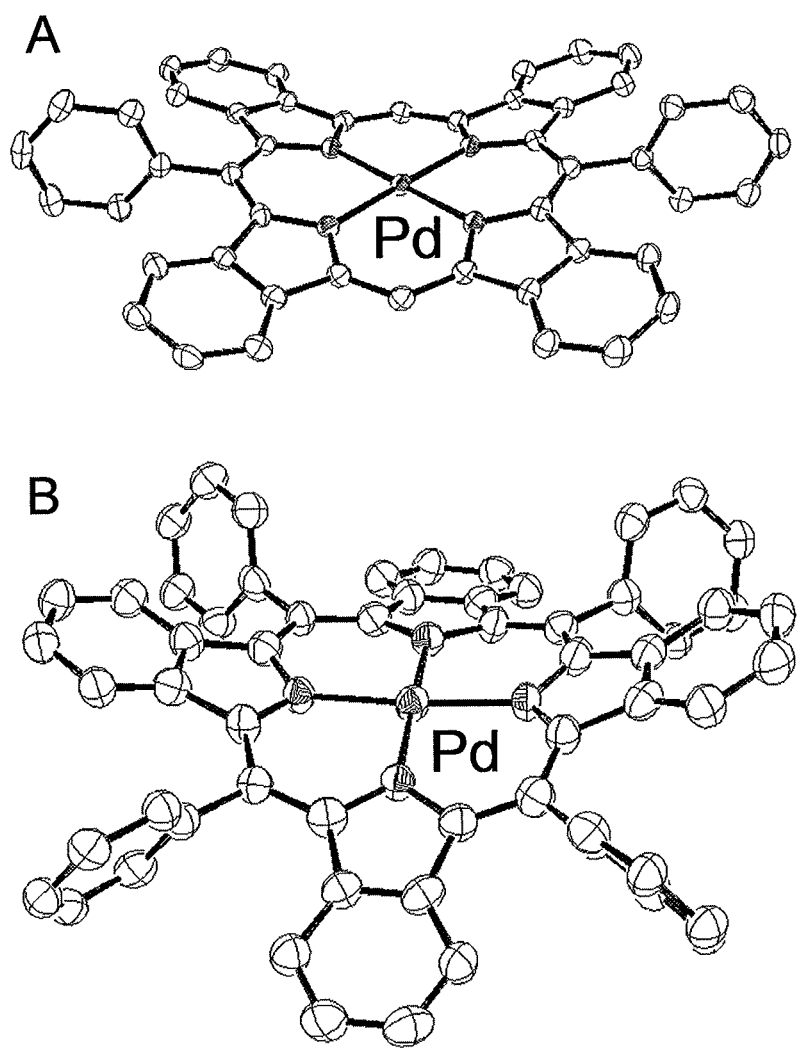
FIGS. 1A and 1B illustrate X-ray crystal structures of PdPh$_2$TBP in FIG. 1A, and PdAr$_4$TBP in FIG. 1B

The present invention provides highly efficient and highly soluble phosphorescent probes suitable for measurements of oxygen in tissue of animals and humans. Inventive probes are surrounded by an inert globular structure, an example of which is derivatized PdTBP (Pd tetrabenzoporphyrins) surrounded by three-dimensional supramolecular structure known as a "dendrimer," which is well understood in the field.

Oxygen levels in biological systems can thus be measured by the phosphorescence quenching method using probes with controllable quenching parameters and defined biodistributions. A general approach is provided to the construction of phosphorescent nanosensors with tunable spectral characteristics, variable degrees of quenching, and a high selectivity for oxygen that are soluble in aqueous or organic solvents (e.g., benzene, toluene, hexane, octane, tetrahydrofurane, mineral oil, and the like), permitting phosphorescence measurements throughout the entire ambient oxygen range: pO$_2$=0-160 mm Hg. The probes are based on bright phosphorescent Pt and Pd complexes of porphyrins and symmetrically extended porphyrins (tetrabenzoporphyrins and tetranaphthoporphyrins).

In certain embodiments of the invention, π-extension of the core macrocycle provides tuning of the spectral parameters of the probes in order to meet the requirements of a particular imaging application (e.g., oxygen tomography versus planar microscopic imaging). Metalloporphyrins are encapsulated into poly(arylglycine) dendrimers, which fold in aqueous environments and create diffusion barriers for oxygen, making it possible to regulate the sensitivity and the dynamic range of the method. The periphery of the dendrimers is modified with poly(ethylene glycol) residues, which enhance the probe's solubility, diminish toxicity, and help prevent interactions of the probes with the biological environment. The probe's parameters were measured under physiological conditions, and the probes were shown to be unaffected by the presence of biomacromolecules.

The performance of the probes was demonstrated in applications, including in vivo microscopy of vascular pO$_2$ in the rat brain.

I. Principles of Phosphorescence Quenching Method and Requirements of In Vivo Oxygen Probes Phosphorescence quenching relies on the ability of molecular oxygen, which is a triplet molecule in the ground state (O$_2$X$^3\Sigma_g^-$), to react with molecules in their excited states, quenching their luminescence. Collisional quenching is much less probable on the time scale of singlet excited states (nanoseconds) than of triplet states (microseconds to milliseconds), making phosphorescence significantly more sensitive to oxygen than fluorescence. Assuming a large excess of oxygen relative to the concentration of triplet emitters—a condition typically met in biological environments—the dependence of the phosphorescence intensity and lifetime on oxygen concentration follows the Stem-Volmer relationship:

$$I_0/I=\tau_0\tau=1+K_{SV}[O_2],\qquad \text{[Equation 1]}$$

where I and τ are the phosphorescence intensity and the lifetime at oxygen concentration [O$_2$] and in the absence of oxygen (I$_0$, τ$_0$); and K$_{SV}$ is the Stem-Volmer quenching constant.

In practice, using lifetime τ as the analytical signal for [O$_2$] is more accurate, because the lifetime is independent of the probe distribution and of any other chromophores present in the biological system. where τ is the phosphorescence lifetime at oxygen concentration at a specific oxygen pressure [pO$_2$]; τ$_0$ is the phosphorescence lifetime in the absence of oxygen [pO$_2$=0]; and k$_q$, is the Stem-Volmer quenching constant. See, Lebedev et al., *ACS Appl. Mater. Interfaces* 1:1292 (2009); Finikova et al., *ChemPhysChem* 9:1673 (2008); Sakad et al., *Nat. Methods* 7:755 (2010); Lecoq et al., *Nat. Med.* 17:893 (2011); Vinogradov & Wilson, In *Designing Dendrimers* Campagna, Ceroni, Puntoriero, Eds.; Wiley: 2012.

Among the attractive features of the phosphorescence quenching technique are its high specificity, submillisecond temporal response, high sensitivity, and relative simplicity of instrumentation. When soluble probes are used, calibration of the method is absolute in a sense that the probes' quenching parameters must be determined only once, and then they may be used thereafter for measurements under similar conditions.

It is customary to express oxygen content in the units of pressure (mm Hg) rather than concentration (M), since in the majority of biological experiments partial pressure of oxygen (pO$_2$) is the actually controlled experimental parameter.

At 298 K and the air pressure of 760 mm Hg (oxygen fraction in the air is 21% or 159.6 mm Hg), air-equilibrated aqueous solutions are 252 µM in $O_2$ (Fogg, et al., *Solubility of gases in liquids*. Wiley, New York, 2001). However, for simplicity the pressure of water vapor above the solution is neglected, although at higher temperatures it will rise and, consequently, the partial pressure of oxygen ($pO_2$) will decrease. This assumes that the Henry's law holds in the physiological range of oxygen concentration: $[O_2]=\alpha \times pO_2$, were $\alpha$ is the oxygen solubility coefficient (M×mm Hg$^{-1}$) for the bulk phase. Considering $K_{SV}=k_2\tau_0$, where $k_2$ is the bimolecular rate constant for the quenching reaction, Equation 1 can be rewritten as:

$$1/\tau = 1/\tau_0 + (k_q)(pO_2) \quad \text{[Equation 2]}$$

where $k_q=\alpha k_2$ and has the units of mm Hg$^{-1}$ s$^{-1}$. Equation 2 contains two parameters specific to the molecule of the probe: constant $k_q$ and lifetime $\tau_0$. Their interplay defines the sensitivity and the dynamic range of the method. For analytical purposes, it is desirable that the measurement parameter, which is the phosphorescence lifetime $\tau$ herein, spans the largest possible interval of values throughout the range of analyte concentrations, assuring highest possible measurement resolution. To quantify the dynamic range of lifetimes, parameter $R=(\tau_0-\tau_{air})/\tau_0$ is used, wherein $\tau_0$ ($pO_2=0$ mm Hg) and $\tau_{air}$ ($pO_2=159.6$ mm Hg) are the maximal and the minimal values of the phosphorescence lifetimes in physiological experiments. Another important parameter is the signal-to-noise ratio (SNR), which is obviously higher for probes with larger emission quantum yields (assuming the same emission wavelengths).

Pt and Pd porphyrins are typically used as phosphorescent chromophores for oxygen measurements in biological systems (vide infra). Triplet lifetimes of Pd porphyrins in deoxygenated solutions at ambient temperatures are in the range of hundreds of microseconds (abbreviations have their normal meaning herein, but microseconds are specifically referred to "µs" or "µsec" herein), and their phosphorescence quantum yields in the absence of oxygen NO are typically 0.05-0.1. (Eastwood et al., *J. Molecular Spectroscopy* 35:359 (1970)). For Pt porphyrins the corresponding values are tens of microseconds and 0.10-0.25 (Id.; Kim et al., *J. Amer. Chem. Soc.* 106:4015 (1984)), respectively. Constants $k_q$ for "unprotected" metalloporphyrins in aqueous solutions are ~3,000 mm Hg$^{-1}$ s$^{-1}$. To illustrate how quenching constants $k_q$, and lifetimes $\tau_0$ affect oxygen measurements, consider two probes, PdP and PtP, representing some arbitrary Pd and Pt porphyrins: $\tau_0$(PdP)=500 µs, $\tau_0$(PtP)=50 µs; $\phi_0$(PdP)=0.05, $\phi_0$(PtP)=0.10, where subscript "0" indicates $pO_2=0$ mm Hg.

When the quenching constant is high, e.g., $k_q=3,000$ mm Hg$^{-1}$ s$^{-1}$, the lifetime of PdP decreases from $\tau_0=500$ µs to $\tau_{air}=2.1$ µs, resulting in a large dynamic range (R≈0.996). However, between about 20 mm Hg and air saturation, the lifetime changes by no more than 3% of the total value, between 16 µs and 2.1 µs. Moreover, already at 10 mm Hg. the probe's quantum yield becomes extremely low ($\phi<0.003$) due to the excessive quenching. Consequently, a probe like PdP is useful only in a very low range of oxygen concentrations, probably not higher than at $pO_2$~5 mm Hg.

Due to its higher quantum yield and shorter $\tau_0$, probe PtP can be used up to about 50 mm Hg (τ=5.9 µs), but above that limit its lifetime also changes very weakly, by no more than ~3 µs. The lifetime dynamic range of PtP (R≈0.96) is not very different from that of PdP; but if the quenching constant were to be reduced or decrease, which is inevitable upon binding of the probe to proteins in vivo (vide infra), this probe would become insensitive to changes in oxygenation.

For higher sensitivity, probes with a greater $\tau_0$ are preferred, but only if their phosphorescence changes gradually instead of being highly quenched already at very low oxygen concentrations. Such adjustment of sensitivity can be achieved by varying constants $k_q$. Overall, it is clear that control over the values of the quenching constants and the ability to keep them unaltered in measurement environments is the key to accurate oxygen measurements. All comparative terms, e.g., higher, lower, increased, decreased, enhanced, reduced, faster, slower, etc, assume their accepted standard dictionary meanings herein, preferable as compared to a stated molecule, probe, compound, or the like.

Phosphorescence quenching by oxygen typically occurs much faster than the diffusion of the reactants and formation of encounter complexes; and in the majority of cases, diffusion can be considered the rate-limiting step for oxygen quenching reaction. (Turro, *Modern Molecular Photochemistry*, University Science Books, Sausalito, Calif., 1991). By altering oxygen diffusion coefficients in the local vicinity of the phosphorescent chromophores, constants $k_q$ can be regulated. Such tuning can be achieved by means of dendritic encapsulation.

Additional requirements for phosphorescent probes for medical imaging of oxygen include lack of toxicity and preferably excretability from the blood upon completion of imaging. Globular uncharged molecules with molecular weights up to about 15 kDa are usually excretable by the kidney (Caliceti et al., *Advanced Drug Delivery Reviews* 55:1261-1277 (2003). If a probe satisfies this criterion and remains confined to the intravascular space (does not diffuse out of the blood vessels), it is likely to be removed from the blood by the kidney-mediated dialysis, and the possibility of long-term toxicity effects can be avoided. Of course, for animal studies, excretability is not as stringent a requirement, whereas confinement to a particular tissue compartment (intravascular, interstitial or intracellular) can be very important. In that case, probes of larger sizes may become advantageous.

This leads to a molecular design comprising a bright phosphorescent chromophore with sufficiently long triplet lifetime $\tau_0$ and a protective jacket, whose purpose is to constrain oxygen diffusion in the local environment of the chromophore. The dendrimer itself must be hydrophobic to permit it to fold (or collapse) in polar solvents, such as water, around the porphyrin. Otherwise, if it were hydrophilic, it would spread branches freely and create no effective barrier for oxygen diffusion to the porphyrin. Importantly, "hydrophobic" does not necessarily mean lipophilic. In other words, a compound that "does not like water" (like the arylglycine (AG) dendrimers defined below) does not mean that it always "likes" every possible type of organic media. For example, the inventors' arylglycine dendrimers fold both in water and in many organic solvents, such as, but not limited to tetrahydrofuran (THF), oils, hexanes, and the like. However, in other organic solvents, such as dimethylformamide (DMF) or dimethylsulfoxide (DMSO), they would spread branches and would not fold. As a result, such dendrimers would not provide a barrier for oxygen in DMF and DMSO; but they would do so in water, THF, oils, alkanes etc.

The periphery of the probe must be hydrophilic and inert in order to prevent interactions with components of the biological system (e.g., bio-macromolecules, cellular membranes). The overall size of the molecule should be large enough to prevent probe leakage through the vascular walls, but yet small enough to allow removal through the kidney, if excretability is desired. Alternatively, the periphery of the probe must be hydrophopbic if the measurement is to be conducted in oils, alkanes, etc.

A novelty of the present invention lies in making the folded molecules soluble. That is accomplished by adding an outer layer to the dendrimer, and it is the outer layer that then takes the probe into solution, even when the dendrimer itself is folded and poorly soluble. Consequently in the present invention, to dissolve a folded dendrimer in water, a hydrophilic outer layer of polyethyleneglycols (PEG) is added to permit dissolution; but when e.g., oils or long alkyl chains are added to the outer layer, the dendrimer is then soluble in liquid organic compounds.

Overall the problem of keeping the diffusional accessibility of the phosphorescent chromophore to oxygen in biological environments constant throughout the studied object and the calibration unchanging, is by far the biggest challenge in the design of phosphorescent oxygen probes. Moreover, this problem is inherent in all methods relying on kinetics of oxygen diffusion. To overcome this difficulty, design of a molecular oxygen sensor entails construction of a well-defined microenvironment around the phosphorescent chromophore in order to isolate it from interactions with other molecules, except for oxygen. Dendritic encapsulation (Hecht & Frechet, *Angewandte Chemie-International Edition* 40:74 (2001); Gorman & Smith, *J. Amer. Chem. Soc.* 122:9342 (2000)) arguably provides one of the most straightforward ways to construct monodisperse, well-defined molecular jackets around luminescent chromophores (Balzani et al., Functional and Hyperbranched Building Blocks, *Photophysical Properties, Applications in Materials and Life Sciences* 228:159 (2003); Ceroni et al., *Progress in Polymer Science* 30:453 (2005)).

II. Phosphorescent Cores of Dendritic Oxygen Probes

The key photophysical properties required for biological oxygen sensing are strong absorption, preferably in the near infra-red region (NIR) of the spectrum (near infrared region of tissue is approximately 600 nm to 1000 nm, but for excitation purposes from ~600 or ~620 to ~900 or ~1000 nm is appropriate) to minimize the interference by the natural tissue chromophores (e.g., heme containing proteins, carotenoids), and strong long-lived phosphorescence in solutions at ambient temperatures. Very few chromophores possess such properties. Among them, metalloporphyrins emit from ($\pi$-$\pi$*) states, and exhibit significantly longer triplet lifetimes (Eastwood et al., *J. Mol. Spectroscopy.* 35:359 (1970)), thus possessing much higher intrinsic sensitivity to oxygen.

Regular meso-tetraarylated Pt and Pd porphyrins with various peripheral substituents can be readily synthesized via, e.g., the Lindsey (Lindsey et al, *J. Organic Chem.* 52:827 (1987)) or Senge (Senge, *Accounts of Chemical Research* 38:733 (2005)) methods. Thermodynamic stabilities of these complexes are extremely high, (Buehler, Ch. 5 in *Porphyrins and Metalloporphyrins*, Smith, K. M. Ed., Elsevier, 1975, New York) entirely precluding release of free metal ions into biological environments and associated toxicity. The major drawback of using regular Pt and Pd porphyrins for in vivo applications is that their absorption bands, the so-called Q-bands, are positioned in the visible range ($\lambda_Q$~520-530 nm; $\epsilon$~20,000 $M^{-1}$ $cm^{-1}$), thus overlapping with absorption of naturally occurring chromophores. Still, absorption in the visible region may be useful in planar wide-field phosphorescence imaging, where less diffuse nature of excitation serves to improve spatial resolution. In addition, absorption near 500 nm overlaps with emission of many two-photon (2P) chromophores, which is useful in construction of FRET-enhanced probes for two-photon oxygen microscopy (vide infra) (Finikova et al., *ChemPhysChem* 9:1673 (2008)).

Many porphyrinoids possess near infrared absorption bands; however, very few have characteristics appropriate for oxygen sensing (Vinogradov & Wilson, *J. Chem. Soc., Perkin Trans. II* 103 (1995)). The most useful today are derivatives of so-called laterally $\pi$-extended (or $\pi$-expanded) porphyrins. Lateral $\pi$-extension of Pt and Pd porphyrins by annealing their pyrrole residues with external aromatic rings results in chromophores with dramatically red-shifted absorption bands and strong room-temperature phosphorescence (Ibid; Tsvirko et al., *Optika i Spektroskopiya (Russ)* 34:1094 (1973); Rozhkov et al., *Inorganic Chemistry* 42:4253 (2003)). Spectra of Pt analogs are very similar in shape, but are blue-shifted by ~10-15 nm as compared to those of Pd counterparts.

An important feature of all porphyrin-based probes is their very large separation between the absorption and phosphorescence, achievable via excitation at the Soret bands (e.g., 9329 $cm^{-1}$ for Pd porphyrins). Efficient $S_2 \rightarrow S_1$ internal conversion, (Tripathy et al., *J. Phys. Chem. A* 112:5824 (2008)) combined with extremely high extinction coefficients of $S_0$-$S_2$ transitions (~3×$10^5$ $M^{-1}$ $cm^{-1}$) makes this pathway superior to the direct $S_0$-$S_1$ excitation in those cases when near UV radiation can be sustained by the biological object.

Until recently, synthesis of $\pi$-extended porphyrins presented a challenging problem. All synthetic methods were based on high temperature condensations between phthalimide (or naphthalimide) and arylacetic acids, or similar donors of benzo- and phenyl-groups (Kopranenkov et al., *J. Gen. Chem. (Russ)* 51:2165 (1981); Edwards et al., *J. Amer. Chem. Soc.* 98:7638 (1976); Ichimura et al., *Inorganica Chimica Acta* 176:31 (1990)). The harsh conditions of condensation (melting at 300-400° C.) allowed for only a few inert substituents, such as alkyl groups or halogens (Kopranenkov et al., *Khimiya Geterotsiklicheskikh Soedinenii* 773 (1988)) to be introduced into the porphyrin macrocycle. In addition, low yields and complex, inseparable mixtures of products made this approach impractical.

The newly emerged approaches to $\pi$-extended porphyrins rely on the Barton-Zard methodology (Barton et al., *Tetrahedron* 46:7587 (1990)) for synthesis of porphyrinogenic pyrroles, which give rise to precursor porphyrins requiring final aromatization. Two methods have been developed into practical synthetic schemes: one making use of retro-Diels-Alder reaction (Ito et al., *Chemical Communications* 1661 (1998); Ito et al., *Chem. Comm.* 893 (2000)), another relying on simple and efficient oxidative aromatization strategy (Finikova et al., *Chem. Commun.* 261 (2001); Finikova et al., *J. Organ. Chem.* 69:522 (2004)). The latter method is being used today to synthesize tetrabenzo- and tetranapthoporphyrins for construction of phosphorescent oxygen probes, as well as in several other applications.

Although meso-tetraarylated $\pi$-extended porphyrins are most common, primarily because of the solubility considerations, meso-unsubstituted tetrabenzoporphyrins (TBP's) and tetranaphthoporphyrins (TNP's), which in fact have higher phosphorescence quantum yields and longer lifetimes, can also be synthesized via the oxidative aromatization method (Finikova et al., *J. Org. Chem.* 70:9562 (2005)). Furthermore, recent introduction of 4,7-dihydroisoindole (Filatov et al., *Europ. J. Org. Chem.* 3468 (2007)) paved a practical route to 5,15-diaryl-TBPs (Filatov, et al., *J. Org. Chem.* 73:4175 (2008)). The latter porphyrins are especially attractive for construction of oxygen probes, as they combine higher emissivity (Lebedev et al., *J. Phys. Chem. A* 112:7723 (2008)) with the possibility of attaching dendrons to the anchor points in the meso-aryl rings, which is lacking in meso-unsubstituted porphyrins. Notably, examples of porphyrin-dendrimers based on 5,15-diarylporphyrins are well known (Dandliker et al., *Angewandte Chemie-International* (Edition in English) 33:1739 (1994); Dandliker et al., *Angewandte Chemie-International* (Edition in English) 34:2725 (1996)).

III. Polyglutamic Pd Porphyrin-Dendrimers

Polyglutamic Pd porphyrin-dendrimers made up the first generation of dendritic oxygen probes (Vanderkooi et al., *J. Biol. Chem.* 262:5476 (1987); Vinogradov & Wilson *J. Chem. Soc., Perkin Trans.* 2:103 (1995); Papkovsky et al., *J. Fluoresc.* 15:569 (2005)). The compounds are described by the general formula, e.g., PdP-(Glu"OH)$_1$, if first generation, where n=1-4 (dendrimer generation) and Glu"OH is the glutamic layer. Similar abbreviations to designate porphyrin dendrimers of different types and generations, terminated by different groups are used herein. But the polyglutamic Pd porphyrin-dendrimers required prebinding to macromolecular carriers (e.g., albumin) in order to enhance their aqueous solubility and bring their quenching parameters ($\tau_0$ and $k_q$, Eq 1) into the range compatible with physiological oxygen concentrations (see Vinogradov & Wilson, In *Designing Dendrimers*, chap 14, Campagna, Ceroni, Puntoriero, Eds.; Wiley: 2012) for discussion). However, foreign albumin was a potential source of toxicity and immunogenic responses.

Introduction of polyglutamic dendritic porphyrins Vinogradov et al., *Chem. Eur. J.* 5:1338 (1999); Vinogradov et al., *Adv. Exp. Med. Biol.* 428:657 (1997); Rietveld et al., *Tetrahedron* 59:3821 (2003), which were generation 2 (gen 2) polyglutamic PD prophyrin dendrimers, known as Oxyphors R2 and G2 (Dunphy et al., *Anal. Biochem.* 310:191 (2002)), offered a partial solution to this problem, and they have been used in many biological studies over the years, wherein dendritic encapsulation was needed to protect the triplet states of Pd porphyrins from oxygen quenching. Polyglutamic probes have high intrinsic aqueous solubility and can be introduced into the blood directly without prebinding to albumin. When in the blood, they form complexes with endogenous albumin, and these complexes serve as ultimate oxygen sensors. But as a result, use of Oxyphors R2 and G2 is limited to albumin-rich environments, such as blood plasma (>2% in albumin by weight). But even in such environments, incomplete binding to albumin, which can be easily encountered at higher probe concentrations (e.g., above ~$10^{-5}$ M), may lead to heterogeneity of the probe signal, skewing the measurement. (Vinogradov et al., *Applied Spectroscopy* 54:849 (2000)). Notably, combinations of polyglutamic probes with polymeric nanoparticle-based carriers have been recently introduced (e.g., Lee et al., *Anal. Chem.* 82:8446 (2010)) which alleviate the necessity of albumin binding and allow oxygen measurements in cultured cells.

Thus, the drawbacks associated with use of dendritic polyglutamic porphyrins clearly show that probes with albumin-independent phosphorescence lifetimes and oxygen quenching constants would greatly simplify data analysis and broaden applicability of the method (e.g., make it possible to take measurements in albumin-free environments). Although polyglutamic dendrimers were limited in use, experiments showed that composition of the dendritic matrix is at least as important for shielding as is the dendrimer size itself, leading to studies of the interplay between the dendrimer composition, size and encapsulating efficiency, as measured by oxygen diffusion and quenching of phosphorescence.

IV. Influence of Size and Composition of Dendritic Matrix on Oxygen Shielding Efficiency In order to determine which dendrimers provide optimal attenuation of oxygen quenching of porphyrin phosphorescence a study was performed (Rozhkov et al., *Macromolecules* 35:1991 (2002)) which involved three types of porphyrin-dendrimers: Fréchet-type poly(aryl ethers) (Hawker et al., *J. Chem. Soc. Perkin Trans.* 11287 (1993)), Newkome-type poly(ether amides) (Newkome et al., *Macromolecules* 24:1443 (1991); Newkome et al., Synlett 53 (1992)), and polyglutamates (Vinogradov et al., *Chemistry-A European J.* 5:1338 (1999)).

Pd-meta-octahydroxyphenylporphyrin and Pd-meta-octa-carboxyphenyl-porphyrin, compatible with either Williamson (Fr) or peptide (Nw, Glu) chemistries, were used as phosphorescent cores. The studies were performed in dimethylformamide (DMF), tetrahydrofuran (THF) and water. To insure appropriate aqueous solubility, termini of the dendrimers were modified with oligoethyleneglycol residues, e.g., PEG (polyethylene glycol) which rendered uncharged molecules soluble both in organic solvents and in water.

In organic solvents, decrease in the quenching rates was found to be consistent with increase in the dendrimer size, and these changes were rather insignificant. As expected, bulkier poly(ether amides) exhibit a stronger effect, but still the decrease in the quenching was only about 75% for G2 dendrimer, whose weight is more than 12 kDa, that is more than 12 times that of the core porphyrin. Notably, in the case of polyglutamic derivatives of PdTCPP, dendrons were attached to the para-positions on the meso-aryl rings of the porphyrin, extending out of the macrocycle instead of covering it from above and below, and thus the shield effect was much weaker for the same size dendrons. A much larger difference in quenching rates was observed in water.

The practical determination was that dendrimers constructed from aromatic building blocks potentially have much higher shielding efficiency in aqueous environments than do other types of dendrimers. In addition, it was determined that in order to prevent interaction of dendrimers with biological macromolecules, their periphery should be modified with PEG residues (vide infra), referred to as "peripheral PEGylation" of the dendrimers.

Other references relating to dendritic macromolocules and their methods of production can be found in U.S. Pat. Nos. 5,418,301; 4,568,737; 5,393,795; 5,256,193; 5,393,797; 5,393,795; 5,393,797; 5,098,475; 5,041,516 and 4,568,737, the entire disclosures of which are incorporated herein by reference. The phosphors employed in, for example, U.S. Pat. No. 5,837,865 (the '865 patent), and by Vinogradov and Wilson, *J. Chem. Soc., Perkin trans.* 2:103-111 (1995), were preferably of the general formula described therein, wherein $R_1$ was hydrogen (H) or substituted or unsubstituted aryl. $R_2$ and $R_3$ were independently hydrogen or are linked together to form substituted or unsubstituted aryl. When $R_2$ and $R_3$ were linked together to form an aryl system, the aryl system was necessarily in a fused relationship to the respective pyrrole substrate. M was $H_2$ or preferably a metal selected from the group consisting of Lu, Pd, Pt, Zn, Al, Sn, Y La, and derivatives thereof, with Pd, Pt and Lu being most preferred.

Accordingly, the prior art formulations were all based on meso-tetraaryl-substituted metalloporphyrins, but the inventors have determined that non-planar deformation of the porphyrin macrocycle resulting from tetra-aryl substitution led to a loss of phosphorescence emission. Thus, the resulting dendritic oxygen probes were effective, but limited for their intended purpose.

V. Protected Dendritic Probes: Oxyphors G4 and R4

Subsequently however, the inventors identified a general approach to protected molecular oxygen probes, which do not require albumin or any other supporting macromolecular carriers or nanocompositions (See, Lebedev et al., *ACS Appl. Mater. Interfaces* 1:1292 (2009); Finikova et al. *ChemPhysChem* 9:1673 (2008); Ceroni, et al., *Photochem. Photobiol. Sci.* 10:1056 (2011)). In these probes, phosphorescent metalloporphyrins are encapsulated inside hydrophobic dendrimers, which form protecting shells, enveloping the chromophores, controlling oxygen diffusion to the excited triplet states, and enabling control over the sensitivity of the approach. Peripheral PEGylation of the dendrimers ensured high aqueous solubility and prevented interactions of the probes with biological macromolecules.

Synthesis and detailed characterization of two new probes, Oxyphors R4 and G4, derived from phosphorescent Pd-meso-tetra-(3,5-dicarboxyphenyl)-porphyrin (PdP) or Pd-meso-tetra-(3,5-dicarboxyphenyl)-tetrabenzoporphyrin (PdTBP), respectively, as reported by Esipova et al, *Anal. Chem.* 83:8756 (published on-line Oct. 11, 2011), herein incorporated by reference. These probes are built according to the above-referenced general scheme, and possess features common for protected dendritic probes, i.e., hydrophobic dendritic encapsulation of phosphorescent metalloporphyrins and hydrophilic PEGylated periphery. The new Oxyphors R4 and G4 are highly soluble in aqueous environments and do not permeate biological membranes. The probes were calibrated under physiological conditions (pH 6.4-7.8) and temperatures (22-38° C.), showing high stability, reproducibility of signals, and lack of interactions with biological solutes were intended for wide use in biological research. However, the probes' structural elements are further optimized for improved yield of synthesis, 1-2 times higher monodispersity of pure monodisperse dendritic oxygen probes, lack of aggregation in aqueous solutions, and overall better chemical stability.

As disclosed above a byproduct of the biological oxygen measurements by phosphorescence quenching using exogenous phosphorescent probes introduced directly into the medium of interest (e.g., blood or interstitial fluid) is singlet, a highly reactive species capable of damaging biological tissue. Consequently, because potential probe phototoxicity is a concern for biological applications studies compared the ability of polyethyleneglycol (PEG)-coated Pd tetrabenzoporphyrin (PdTBP)-based dendritic nanoprobes of three successive generations to sensitize singlet oxygen. As a result, it was demonstrated that the size of the dendrimer has practically no effect on the singlet oxygen sensitization efficiency in spite of the strong attenuation of the triplet quenching rate with an increase in the dendrimer generation.

Nevertheless, in spite of their ability to sensitize singlet oxygen, the phosphorescent probes were found to be non-phototoxic when compared with the commonly used photodynamic drug Photofrin in a standard cell-survival assay. (Ceroni et al., *Photochem. Photobiol. Sci.* 10:1056-1065 (2011)). The lack of phototoxicity is presumably due to the inability of PEGylated probes to associate with cell surfaces and/or penetrate cellular membranes. In contrast, conventional photosensitizers bind to cell components and act by generating singlet oxygen inside or in the immediate vicinity of cellular organelles. Therefore, PEGylated dendritic probes are safe to use for tissue oxygen measurements as long as the light doses are less than or equal to those commonly employed in photodynamic therapy.

One of the probes, Oxyphor G4 was applied to imaging of oxygen distributions in tumors, both intravascularly and in the interstitial space. The probe allowed dynamic visualization of the tissue $pO_2$ levels in the tumor and in the surrounding muscle, as oxygenation responded to changes in the depth of anesthesia. The phosphorescence from the probe also could be detected in trans-illumination geometry, i.e., through the whole body of the animal, thus demonstrating feasibility of in vivo full body oxygen tomography.

VI. Effect of the Dendrimer Outer Layer

Although it is critically important that quenching properties of phosphorescent probes do not change in the presence of blood plasma proteins and other biological macromolecules, quenching constants of all carboxylate-terminated porphyrin-dendrimers were found to be highly sensitive to albumin. For example, $k_q$, of gen 2 Frechet-type porphyrin dendrimer in albumin solution (2% by mass) is five times lower (30 mm $Hg^{-1}$ $s^{-1}$) than that in the albumin-free aqueous buffer (151 mm $Hg^{-1}$ $s^{-1}$) (Gorman et al., *J. Amer. Chem. Soc.* 122:9342 (2000)). To the contrary, however, quenching of porphyrin-dendrimers modified with oligoethyleneglycol residues (PEG350, Av. MW=350) appeared to be unaffected by serum proteins. Thus, $k_q$ of the PEGylated analogue of gen 2 Fréchet-type porphyrin dendrimer was found to have the same value (130 mm $Hg^{-1}$ $s^{-1}$) in the presence and in the absence of albumin (Estrada et al., *Optics Letters* 33:1038 (2008)).

Thus, it was important to distinguish between the effect of hydrophobic dendrons and the effect of external PEG residues. While the latter also contribute to the protection from quenching, especially at early dendritic generations, the net effect of PEG is very small, as noted above, compared to the shielding by dendritic branches. Moreover, the PEG effect rapidly levels off with extension of linear chains. It was shown that external PEG chains as large as 300,000 Da have practically no effect on oxygen quenching constants of these molecules. Moreover, in addition to being able to prevent interactions of dendrimers with proteins, peripheral PEG groups also strongly affect biodistribution and rate of excretion of dendritic macromolecules (Newkome, supra, 1992).

VII. Aryl-Glycine Dendrimers and Fully Protected Phosphorescent Probes

Among known dendrimers with aromatic backbones, dendritic arylamides were very attractive because of their high chemical stability, low cost and effective protocols available for their assembly. In particular, arylamide dendrimers based on 5-aminoisophthalic acid (5-AIPA) were selected to make the focal functionality more reactive and to simultaneously increase the flexibility of the dendritic backbone by extending the amino-end of the 5-AIPA molecule by adding a flexible fragment, terminated with an aliphatic amine. This possibility was explored by constructing aryl-glycine (AG) dendrons and dendrimers (Vinogradov, *Organic Letters* 7:1761 (2005)). The following abbreviations are used to designate aryl-glycine dendrons and dendrimers. Dendrons were designated X-AGnR, where AG denotes the dendritic aryl-glycine skeleton, n is the dendrimer generation number, X is the focal functionality and R is the terminal group. Dendrimers were designated C-(AGnR)$_m$, where C denotes the dendrimer core, AG denotes the dendritic aryl-glycine skeleton, n is the generation number, R is the terminal group and m is the number of dendritic wedges attached to the core.

The developed synthesis of AG dendrons relies on the classic Fischer's haloacyl halide method (Miller et al., Chem. Mater. 2:346 (1990)) for the synthesis of building blocks. Synthesis of AG-dendrons in principle also can be implemented using the Fischer's method, however, a more robust scheme is based on a coupling-deprotection sequence employing the peptide-coupling reactions of Lebedev et al., ACS Applied Materials & Interfaces 1:1292 (2009)). See also synthesis and peptide-coupling reactions described in greater detail in Vinogradov & Wilson, In Designing Dendrimers, chap 14, Campagna, Ceroni, Puntoriero, Eds.; Wiley: 2012).

Each step of the sequence was carefully optimized in order to insure maximal yields and monodispersity of the probes. Porphyrins modified with $AG^1$ and $AG^2$ (aryl-glycine, first and second generation) dendrons could be isolated in high purity, but modification of porphyrins with $AG^3$-dendrons (third generation) proved extremely challenging, always yielding mixtures of dendrimers with six, seven and eight dendritic branches. The peripheral ester groups were hydrolyzed using a special two-step procedure (Lebedev et al., supra, 2009), which in parallel destroys unreacted dendrons, making it possible to entirely avoid chromatographic purifications. The resulting peripheral carboxyl groups on the dendrimers are esterified with PEG residues of the desired length, and simple re-precipitation from THF upon addition of diethyl ether produced pure PEGylated dendrimers. The magnitude of the attenuation effect is similar to that of poly(aryl ether) dendrimers. As a result quenching constants and lifetimes of gen 2 Pd porphyrin-dendrimers are well suited for biological oxygen measurements. These probes exhibit good dynamic range and excellent sensitivity. For example, in the case of PdP-based gen 2 dendrimer the relative sensitivity coefficient R (vide supra) is as high as 0.9. Moreover, PEG-coated AG porphyrin-dendrimers exhibited a property that their oxygen quenching constants $k_q$ and lifetimes $\tau_0$ are completely insensitive to the presence of biological macromolecules.

VIII. Improvements in the "Next Generation" of Oxygen Sensors: 5,15-Diaryl and Meso-Unsubstituted Porphyrin Embodiments.

A) Increased Emission Output (Quantum Yield) of Phosphorescent Porphyrin-Based Probes.

Systematic structure/property comparisons between differently substituted porphyrins, have demonstrated that dendritic oxygen probes can be constructed using Pd meso-unsubstituted or 5,15-diaryl-substituted π-extended porphyrins (recognized as meaning that the aromatic macrocycle of the porphyrin is extended by way of extending its π-electronic system But the 5,15-diaryl-substituted π-extended porphyrins have significantly higher phosphorescence quantum yields (up to 50% greater) than tetraaryl π-extended porphyrins, and long enough triplet lifetimes for higher oxygen sensitivity.

Probes based on π-extended porphyrins are optimal for tomographic tissue oxygen imaging applications (Apreleva et al., Applied Optics 45:8547-8559 (2006); Apreleva et al., Optics Letters 33:782-784 (2008)), where excitation in the near infrared range (NIR) is required. For high-resolution microscopy applications, excitation in the visible range is preferred (Golub et al., Am. J. Physiol.-Heart and Circulatory Physiol. 294 (1):H21 (2008); Yaseen et al., J. Cerebral Blood Flow and Metabolism 29:S381-S393 (2009); Yaseen et al., Opt. Express 17:22341-22350 (2009)).

In both cases, however, increase in the phosphorescence quantum yield is an important objective. Pd meso-tetraaryl-porphyrins have their quantum yields at zero-oxygen in the range of 0.02-0.08 and triplet lifetimes of 300-700 μs, depending on the type of π-extension, i.e., tetrabenzo-extension or tetranaphtho-extension with respect to the basic 18-tetrapyrrolic macrocycle (Rozhkov et al., Inorg. Chem. 42:4253-4255 (2003); Rogers et al., J. Physical Chem. A 107:11331-11339 (2003)). Analogous Pt porphyrins have the quantum yields of 0.10-0.20, when measured by currently approved measurement techniques, and their lifetimes are 30-60 μs.

The inventors' detailed photophysical, structural and computational studies were conducted to delineate the interplay between radiative and non-radiative triplet deactivation processes in Pd porphyrins and tetrabenzoporphyrins (see Lebedev et al., J. Physical Chem. A, 112:7723-77336 (2008)). In fact, non-planar distortions of the porphyrin macrocycle were shown to diminish the triplet emission yield of PdTBP's competing non-radiative triplet-to-singlet ground state transitions, i.e., intersystem crossing. This is because the lifetime of the PdTBP triplet state in the absence of oxygen increases with dendritic generation, thus compensating for the concomitant decrease in the rate of quenching. In fact, non-planar distortions of the porphyrin macrocycle were shown to diminish the triplet emission yield of PdTBP's by increasing the rate of $T_1 \rightarrow S_0$, referring to the internal, non-radiative quenching of the triplet state ($T_1$) (returning it to the ground state ($S_0$). Increase in this non-radiative pathway decreases phosphorescence emission. However, this effect is considerably less pronounced than in regular non-extended porphyrins (see FIG. 1). FIG. 1 clearly shows much less non-planar distortion of the macrocycle in the case of PdPh2TBP. Photophysical measurements show that non-planar deformations have deleterious effect on the porphyrin triplet emissivity. Therefore, even highly saddled tetraaryl-TBP's, which are used as cores in current probes, are able to phosphoresce.

It was also determined by the inventors' studies that Pd (and Pt) TBP's without meso-substituents (Finikova et al., J. Org. Chem. 70:9562-9572 (2005A)) and 5,15-diaryl-TBP's (Filatov et al., J. Org. Chem. 73:4175-4185 (2008)) have much higher emission quantum yields than the corresponding tetraarylporphyrins. In the case of meso-unsubstituted PtTBP's, phosphorescence quantum yields reach as high as 0.5 at room temperature, by currently accepted measuring techniques. The same trends are characteristic of TNP's.

Figure 2:
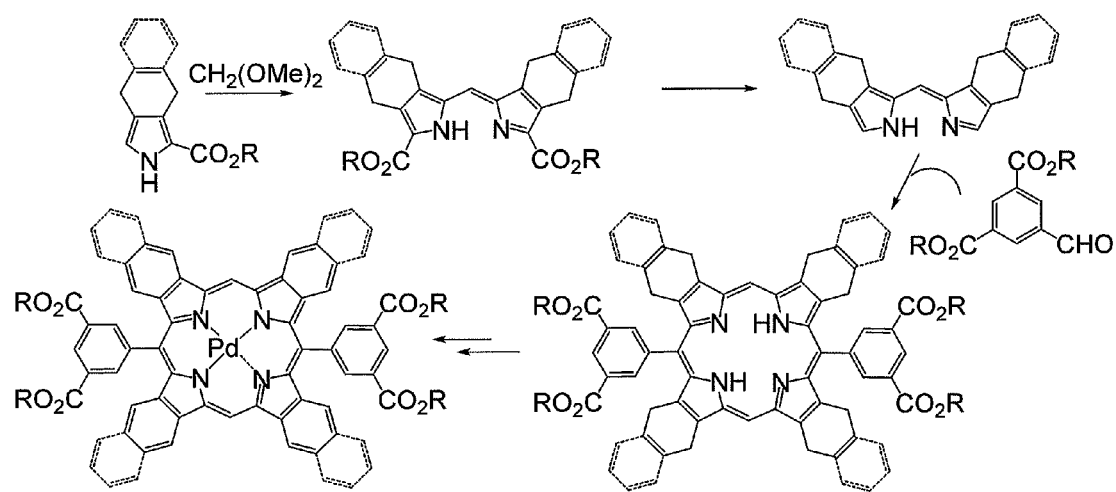
FIG. 2 illustrates an exemplary synthesis of 5,15-diaryltetrabenzo- and tetranaphthoporphyrins.

Based on these findings, Pt and Pd meso-unsubstituted, as well as 5,15-diarylsubstituted TBP's and TNP's, are used as for construction of embodiments of the new generation probes of the present invention. The synthesis of 5,15-diarylsubstituted porphyrins is based on the recently developed 4,7-dihydroisoindole method (Filatov et al., (2008) supra; Cheprakov et al., J. Porphyrins and Phthalocyanines 13:291-303 (2009)), and on the analogous strategy developed earlier for the synthesis of precursors of TNP's (Finikova et al., (2005A) supra; Finikova et al., J. Org. Chem. 68:7517-7520 (2003); Finikova et al., J. Org. Chem. 70:4617-4628 (2005B)). See, FIG. 2.

In one embodiment of the present invention, the porphyrinogens are assembled using the 2+2 (Filatov et al., "Synthesis of 5,15-diaryltetrabenzoporphyrins," J. Org. Chem. 73:4175. (2008)) and oxidized by DDQ (dichlorodicyano-1,4-benzoquinone) into the target precursor tetracyclo-hexenoporphyrin (TCHP) (Ibid). After insertion of Pd (or Pt), the TCHP is oxidized, also by DDQ, into target TBP's (Finikova et al., "Novel versatile synthesis of substituted tetrabenzoporphyrins," J. Org. Chem. 69:522 (2004)).

Synthesis of meso-unsubstituted TBP's and TNP's with substituents in the fused rings has been previously developed (Finikova et al., "Synthesis and luminescence of soluble meso-unsubstituted tetrabenzo- and tetranaphtho[2, 3]porphyrins," *J. Org. Chem.* 70:9562 (2005)). However, these positions are hindered sterically, especially with respect to the attachment of bulky dendritic ligands, required for "protection" of the porphyrin core from excessive oxygen quenching.

Figure 3:
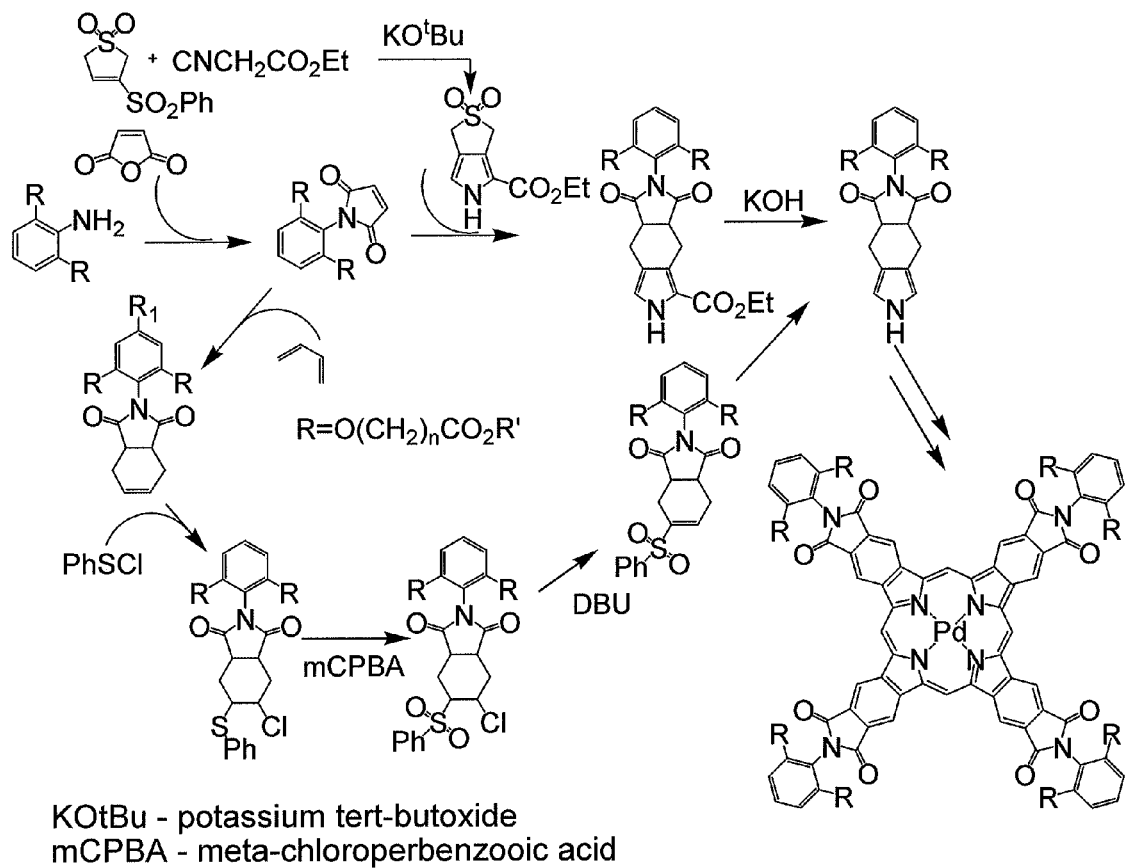
FIG. 3 illustrates an exemplary synthesis of meso-unsubstituted TBP.

In an embodiment of the invention, the scheme depicted in FIG. 3 is used to synthesize meso-unsubstituted TBP's with appropriately positioned anchor groups as disclosed. The scheme shows two routes, sharing maleimide as a common precursor. One route was based on the modified Barton-Zard synthesis of sulfolenolpyrrole (a method of pyrrole synthesis by a cyclization reaction between a nitroalkene and α-isocyanoacetate under base conditions) developed previously by Vicente et al., *Tetrahedron Letters* 38:3639-3642 (1997). A second route was also feasible; however, conditions of the Barton-Zard reaction (Barton, Zard, "A new synthesis of pyrroles from nitroalkenes,"*J. Chem. Soc.* 1098 (1985)), needed to be adjusted for each specific case, as its outcome is likely to be affected by the presence of aromatic imide group. The stability of this imide depends on the substituents R and their positions (given that electron-withdrawing substituents in 3,5-positions will destabilize the imide with respect to hydrolytic cleavage). Accordingly, to insure better protection of meso-unsubstituted porphyrins already at early dendritic generations in at least one embodiment, 2,6-substituents were used, which direct the dendrons under and above the porphyrin plane.

B) Improved Procedure for Dendrimerization of Porphyrins.

Embodiments of the invention have shown that attachment of extension linkers to the anchor groups on either meso-aryl rings or directly on porphyrin macrocycle greatly facilitates coupling of the protecting dendrons. Specifically, extension of carboxylic groups with γ-aminobutyrate linkages ("extension arms") permitted high yield synthesis of monodisperse dendritic oxygen probes or improved sensitivity and higher purity (See, basic photophysical studies as a foundation for determining the significantly higher phosphorescence quantum yields of the 5,15-diaryl-substituted π-extended porphyrins, as compared with tetraarylporphyrins by Esipova et al., "Two new "protected" oxyphors for biological oximetry: properties and application in tumor imaging," *Analytical Chem.* 83:8756 (published on-line Oct. 11, 2011).

Dendrimerization of phosphorescent porphyrins includes hydrolysis of the peripheral ester groups on the porphyrin, attachment of dendrons, hydrolysis of their peripheral esters on the dendrons and PEGylation of the resulting free carboxyl groups. See, FIG. 3. These methods have been developed by the inventors and described in their previous patents cited above, and incorporated herein by reference. One critical improvement, however, that was only recently established, relates to the yield and purity-limiting step in the synthesis—that is, attachment of the bulky dendritic substituents to the porphyrin core. This step typically proceeds via one of the standard peptide coupling reactions, or any other suitable chemistry. Yet the steric hindrance imposed by large folded dendritic groups impedes the reaction. However, if the anchor groups are extended by flexible linkers, bulky substrate react slowly because of unfavorable steric reasons, and thus the actual reaction sites are placed at a larger distance from one-another, they become much more accessible to nucleophilic attack. Consequently, the resulting reaction occurs with higher rate, i.e. complete dendrimerization is reached overnight (approx. 24 hours), as opposed to 7 days in the case of porphyrins without extension arms, and provides clean octa-dendrimerized porphyrin, as opposed to mixture of hexa-, hepta- and octa-dendrimerized porphyrins (imperfect contaminating dendrimers) that were obtained in the case of porphyrins without extension arms.

Figure 4:
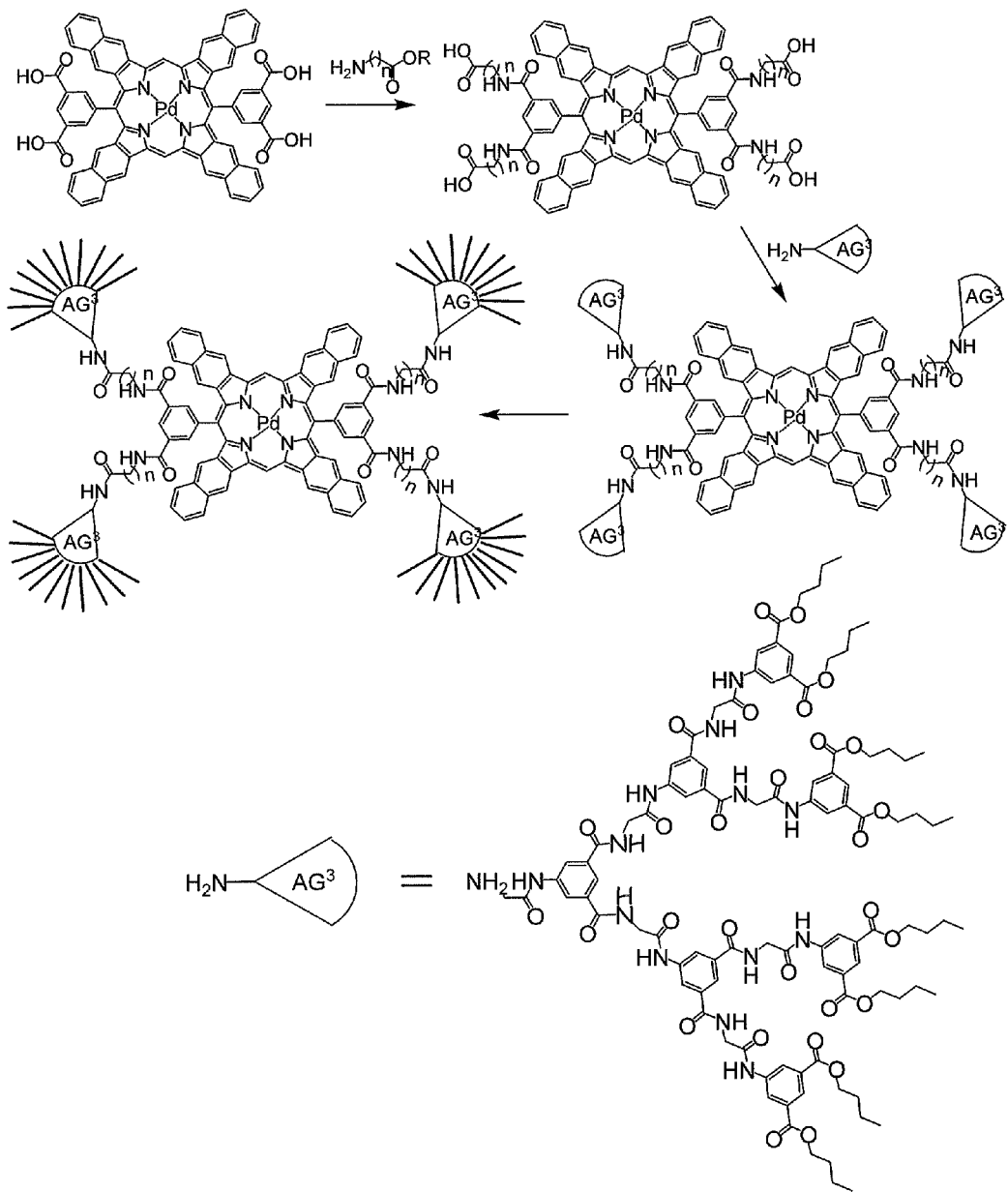
FIG. 4 illustrates exemplary dendrimerization of porphyrins: i) peptide coupling; ii) hydrolysis.

The overall scheme of the synthesis is shown in FIG. 4 for the case of 5,15-diaryl-p-extended porphyrins (vide supra). The extension step is the first step in the reaction sequence, and the addition of AG3 elements (third generation (Gen 3) arylglycine dendrimers.

C) Increase in the Excitation Cross-Sections of the Probe Via Intramolecular Fluorescence Resonance Energy Transfer (FRET).

One approach to enhancing production of excitement cross-sections in metalloporphyrins without directly altering their electronic properties involves harvesting the excitation energy by an electronically separate antenna and to pass it onto the phosphorescent core via intramolecular Förster-type resonance energy transfer (FRET) (See, Briñas et al., *J. Amer. Chem. Soc.* 127:11851 (2005)). In such an antenna-core system constructed around a dendrimer, the latter regulates the rate of oxygen diffusion to the core, just as in the regular dendritic probes (see above), while the dendrimer termini control the probe bio-distribution.

Resonance energy transfer is the radiationless transmission of an energy quantum from its site of absorption to the site of its utilization in the molecule, or system of molecules, by resonance interaction between chromophores, over distances considerably greater than interatomic distance, without conversion to thermal energy, and without the donor and acceptor coming into kinetic collision. The donor is the marker that initially absorbs the energy, and the acceptor is the chromophore to which the energy is subsequently transferred. (from Van Der Meer, Coker, and Chen, *Resonance Energy Transfer Theory and Data*, VCH, New York, 1994).

Förster (Fluorescence) resonance energy transfer (FRET), resonance energy transfer (RET) or electronic energy transfer (EET), is a mechanism describing energy transfer between two chromophores. [1] A donor chromophore, initially in its electronic excited state, may transfer energy to an acceptor chromophore through nonradiative dipole-dipole coupling. [2] The efficiency of this energy transfer is inversely proportional to the sixth power of the distance between donor and acceptor making FRET extremely sensitive to small distances. [3] Measurements of FRET efficiency can be used to determine if two fluorophores are within a certain distance of each other. [4] Such measurements are used as a research tool in fields including biology and chemistry. When both chromophores are fluorescent, the term "fluorescence resonance energy transfer" is often preferred, although the energy is not actually transferred by fluorescence. In order to avoid an erroneous interpretation of the phenomenon that is always a nonradiative transfer of energy (even when occurring between two fluorescent chromophores.

FRET is analogous to near field communication, in that the radius of interaction is much smaller than the wavelength of light emitted. In the near field region, the excited chromophore emits a virtual photon that is instantly absorbed by a receiving chromophore. These virtual photons are undetectable, since their existence violates the conservation of energy and momentum, and hence FRET is known as a radiationless mechanism. Quantum electrodynamical calculations have been used to determine that radiationless (FRET) and radiative energy transfer are the short- and long-range asymptotes of a single unified mechanism. Jablonski diagrams illustrate the electronic states of a molecule and the transitions between them. The states are arranged vertically by energy and grouped horizontally by spin multiplicity (Jabłoński, Aleksander "Efficiency of Anti-Stokes Fluorescence in Dyes" *Nature* 131:839-840 (1933)).

1) Theoretical basis of FRET:

When the donor probe is a fluorescent molecule, and when light excites the fluorophore at an appropriate wavelength (250-500 nm), its electrons jump from the ground state (S) to a higher vibrational level (S, $S_0$, $S_1$, etc). Within picoseconds these electrons decay to the lowest of these vibrational levels (S) and then decay more slowly (nsec) to one of the S states and a photon of light is emitted whose wavelength is longer than that of the exciting wavelength. The acceptor probe can be fluorescent or non-fluorescent.

The FRET efficiency depends on many physical parameters that can be grouped as follows:

The donor probe must have a high quantum yield.

The spectral overlap of the donor emission spectrum and the acceptor absorption spectrum. The emission spectrum of the donor probe must overlap considerably the absorption spectrum of the acceptor probe (overlap integral).

There is an appropriate alignment of the absorption and emission moments and their separation vector (embodied in kappa square).

The distance between the donor and the acceptor. The donor and acceptor must be within $1\pm0.5\times r_o$ from each other, when r=donor-to-acceptor separation distance.

The relative orientation of the donor emission dipole moment and the acceptor absorption dipole moment.

Accordingly, FRET efficiency relates to the quantum yield and the fluorescence lifetime of the donor molecule as follows (See, e.g., Majoul et al. (2006). "Practical Fluorescence Resonance Energy Transfer or Molecular Nanobioscopy of Living Cells." In Fawley, *Handbook Of Biological Confocal Microscopy* (3rd ed.). New York, N.Y.: Springer. pp. 788-808). In fluorescence microscopy, fluorescence confocal laser scanning microscopy, as well as in molecular biology, FRET is a useful tool to quantify molecular dynamics in biophysics and biochemistry, such as protein-protein interactions, protein-DNA interactions, and protein conformational changes. For monitoring the complex formation between two molecules, one is labeled with a donor, and the other with an acceptor. The FRET efficiency is measured and used to identify interactions between the labeled complexes. After excitation, the states of the antenna ($^aS_{2P}$) are populated and have internally converted into the lowest excited singlet state $^aS_1$, the excess energy is transferred to the core.

The Förster energy transfer mechanism assumes that the fluorescence ($^aS_1 \rightarrow ^aS_0$) of the donor (2P antenna) overlaps with an absorption band $^cS_n \leftarrow ^cS_0$ (n=1, 2 . . . ) of the acceptor (core). Therefore, the core must possess linear absorption band(s) somewhere in the region extending to the red from 400 nm. Exact positions of these bands are defined by the Stokes shift of the fluorescence of the antenna relative to its absorption at 400 nm. The FRET from the antenna to the core results either in the population of its singlet excited state $^cS_1$, which is depopulated via the intersystem crossing ("isc") to yield the triplet state $^cT_1$, resulting in either oxygen quenching or phosphorescence. Thus, FRET efficiency is the quantum yield of the energy transfer transition, i.e., the fraction of energy transfer event occurring per donor excitation event. There are several ways of measuring the FRET efficiency by monitoring changes in the fluorescence emitted by the donor or the acceptor or as the variation in acceptor emission intensity (Clegg, R. (2009). In Gadella, Theodorus, *FRET and FLIM Techniques. Laboratory Techniques in Biochemistry and Molecular Biology*, Vol. 33, Elsevier. pp. 1-57). When the donor and acceptor are in proximity (1-10 nm) due to the interaction of the two molecules, the acceptor emission increases because of the intermolecular FRET from the donor to the acceptor.

Figure 5A:
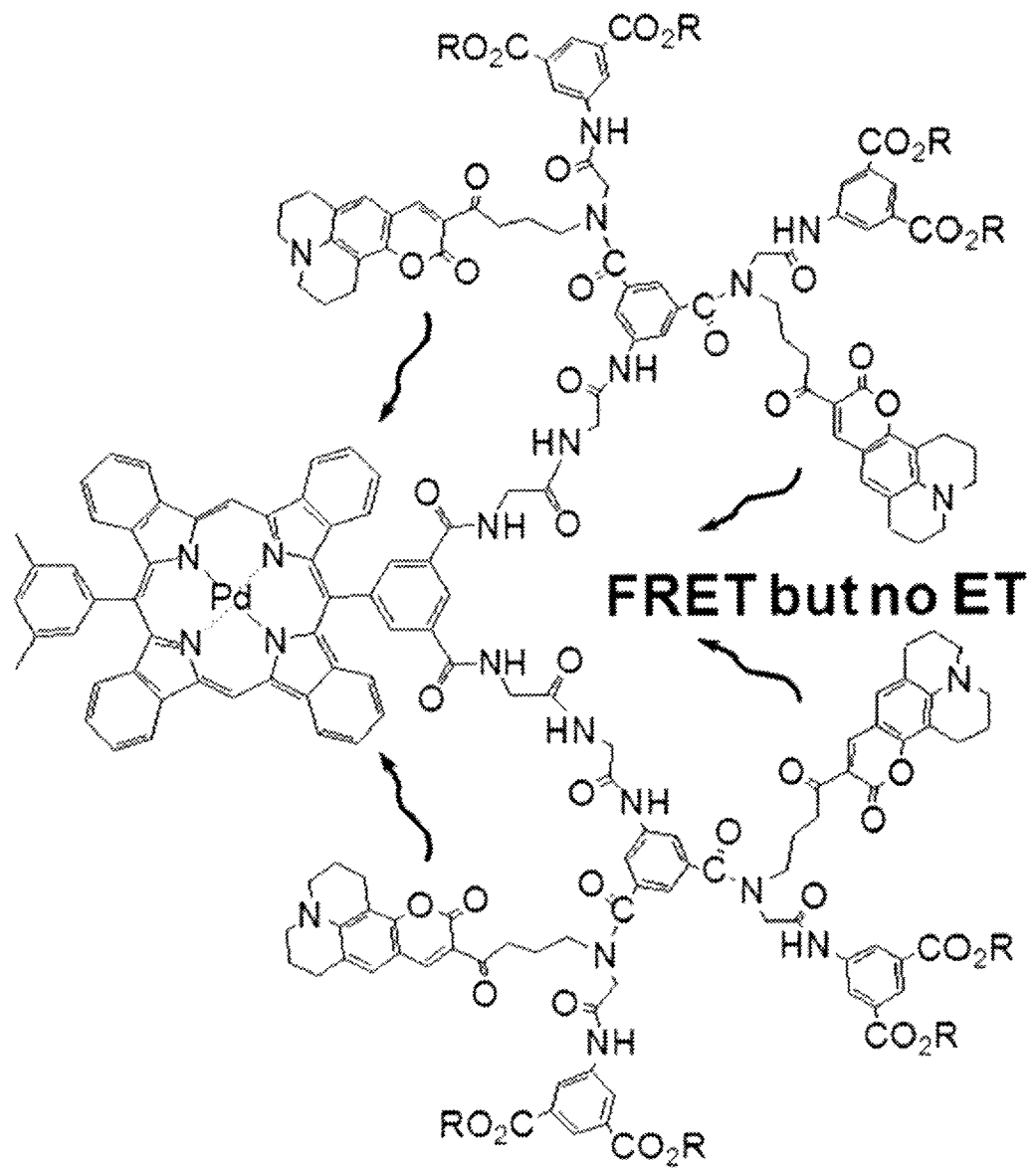
FIGS. 5A-C illustrate in FIG. 5A an exemplary design of FRET-enhanced probes.
Figure 5B:
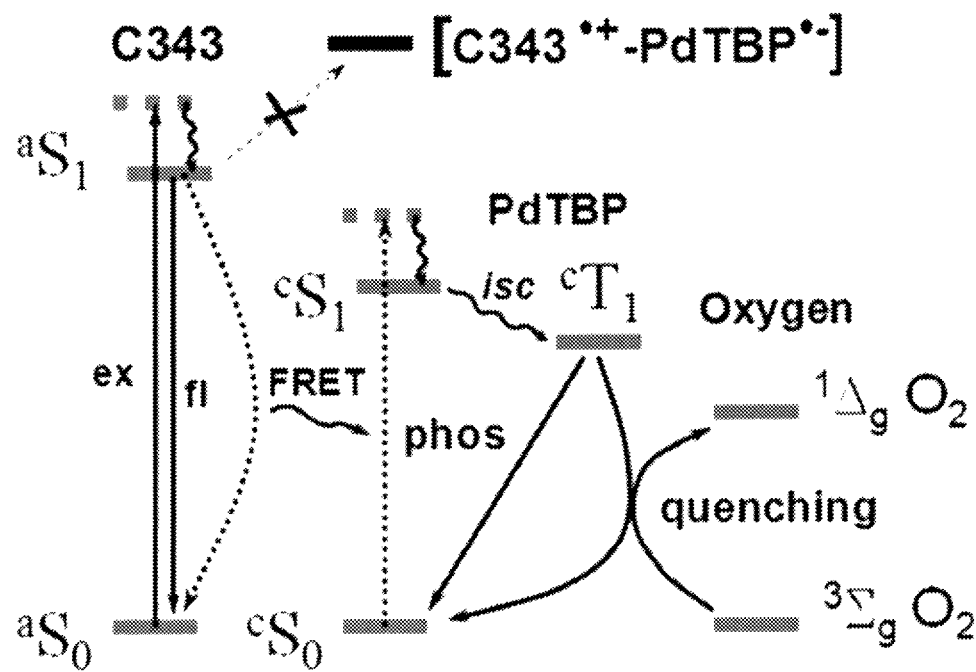
Figure 5C:
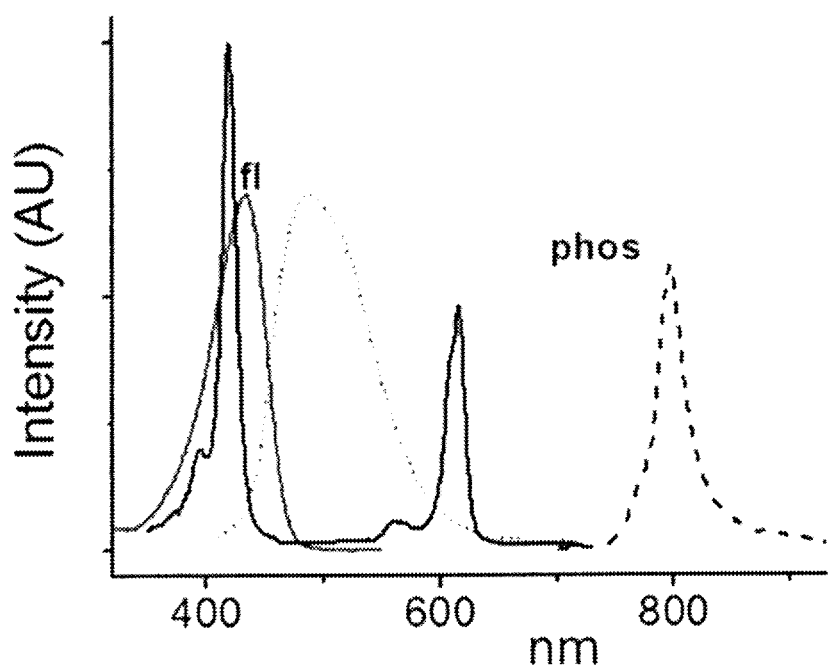

An example of the intramolecular Fluorescence Resonance Energy Transfer (FRET) method is shown in FIG. 5. Aryl-glycine dendrimers are modified by including functional groups into their interior. Although coumarins (Briñas et al., *J. Amer. Chem. Soc.* 127:11851 (2005)) are rather moderate 2P absorbers, their 2PA cross-sections (tens of GM units) are still higher than of Pt porphyrins, and the emission of some coumarins, for example of coumarin-343 (C343), is compatible with Q-band absorption of Pt porphyrins ($\lambda_{max}$=510 nm, $\epsilon$=25,800 M$^{-1}$ cm$^{-1}$), suggesting high efficiency FRET. C343 fluoresces with quantum yield $\phi_n$=75 in DMF and its $\sigma_2$ value is about 25 GM. Briñas et al. showed four C343 moieties could be attached to PtTCPP (Pt meso-tetra(4-carboxyphenyl)porphyrin") via ethylenediamine linkers using standard peptide chemistry, giving a simple FRET-enhanced two-photon-absorbing phosphorescent probe.

In this case, coumarin-343 (C343) units operate as antenna chromophores to enhance the absorption of dendritic probes. The spectral overlap between fluorescence of C343 and the Q-band absorption of PdTBP is not large, and Förster donor-to-acceptor separation distance r distance (see Equation 2 above) for this pair is estimated to be ~10 Å. However, C343 units in the molecule of FIG. 5 were separated from the porphyrin by Förster distances not more than $r_0$, and FRET occurred with >95% efficiency. The residual C343 fluorescence, which is not oxygen-independent, provided the reference signal. The absorption of C343 will extend the absorption of Soret band of PdTBP. (The UV-visible electronic absorption spectrum of a typical porphyrin macrocycle consists of a strong transition to the second excited state ($S_0 \rightarrow S_2$), exhibiting an intense feature (extinction coefficient >200.000) at about 400 nm (the Soret or B band), and a weak transition to the first excited state ($S_0 \rightarrow S_1$) at about 550 nm (the Q band).) See the Gouterman four orbital model of the absorption spectra of porphyrins, e.g., Milgrom, "The Colours of Life: An Introduction to the Chemistry of Porphyrins and Related Compounds," Oxford, 1997; *The Porphyrins*, ed. D. Dolphin, Academic Press, New York, 1978). This enhancement enables use of several available laser bands (different wavelength lasers for excitation).

Finally, C343 contains an amino-group, whose free electron pair should provide a good target for singlet oxygen, which is produced as a result of phosphorescence quenching, thus decontaminating and detoxifying the measurement environment. Singlet oxygen can be generated during quenching of phosphorescence, and this would inactivate any singlet oxygen that is formed before it can leave the region of the phosphor. Importantly, since C343 is an aromatic amine (aniline), it is not protonated under physiological conditions. Indeed, the fluorescence spectra of C343-based probes, including two-photon-enhanced phosphorescent probes (Brinas et al., *J. Amer. Chem. Soc.* 2005, 127:11851-11862 (2005); Finikova et al., *J. Physical Chem. A* 111:6977-6990 (2007); Finikova et al., *Chem. Phys. Chem.* 9:1673-1679 (2008A)) are not affected by pH changes in the physiological range. This would not be the case if the amino-group were protonated.

D) Dendritic Phosphorescent Probes are Suitable for Oxygen Measurements in Liquid Organic Media, e.g., Organic Solvents or Oils.

Figure 6:
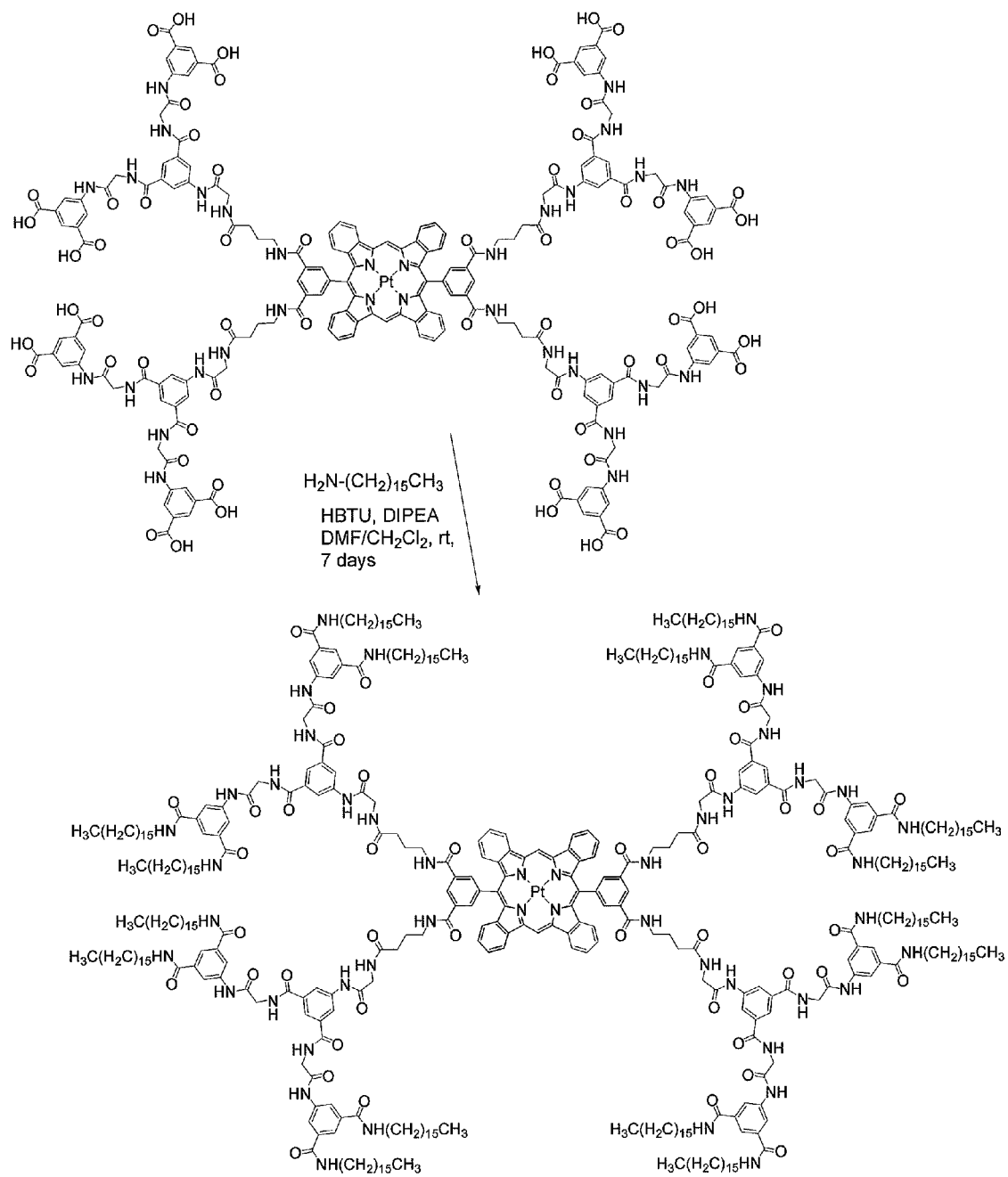
FIG. 6 illustrates an exemplary dendritic phosphorescent probe modified with hydrophobic residues to allow oxygen measurements in liquid organic solutions, e.g., saturated alkanes, mineral oils etc.

The present invention provides oxygen sensors that can be designed to be dissolved in water media (for use in biological systems) or designed to be dissolved in organic media (for use in specialized oxygen sensors for any process in which organic media can be used, including those requiring organic media. This is a specific section for those that would best be dissolved in organic media, for which the external shell would need to different from those used in water based media. To achieve solubility of the dendritic probes in organic media the termini of the dendrimers (e.g., carboxyl groups) are amidated using 1-aminoalkanes, or esterified using 1-hydroxyalkanes to create a supramolecular hydrophobic outer layer (FIG. 6). The chemistry for this modification and the purification protocols closely resembles the above-discussed procedures for covering dendrimer surfaces with PEG groups. But in accordance with addition of the supermolecular hydrophobic outer layer, the resulting probes showed extremely high solubility in saturated hydrocarbons, aromatic mineral oils and other organic solvents, whereas without attachment of the new outermost layer the probe remains completely insoluble in such liquids.

In order to keep the Stern-Volmer oxygen quenching constant of the probe suitable for oxygen measurements in the physiological $pO_2$ range, polyarylglycine or other polyamide dendrimers (namely, polyglutamic, polyesteramide, polyarylamide) have been tested. These dendrimers fold well in aqueous, as well as in organic environments, serving to attenuate oxygen access to the phosphorescent cores. Thus, essentially the same dendrimers can be used for both aqueous and hydrophobic environments, and only the outer layers ("supramolecular") needs to be changed.

In sum, methods are provided for substantially improving the currently available oxygen sensitive phosphors by increasing the quantum efficiency (phosphorescence intensity) and extending their range of applicability through making a class of oxygen sensors for measurements in organic media. Thus, methods are provided in the present invention for synthesizing new porphyrin constructs in which the porphyrin is made less flexible and more planar, changing with decrease internal quenching and thereby increasing the phosphorescence emission used for oxygen sensing. Additional methods are provided for structurally modifying the dendrimer used to encapsulate the porphyrin phosphor to provide for internal quenching of any singlet oxygen formed while measuring oxygen. Moreover, in the present invention it is the outer layer that controls the solubility of the probe as a whole. If the probe needs to be soluble in water—a water-soluble outer layer is added; whereas if the probe needs to be soluble in organic media—an outer layer is added, making it compatible with organics. The inventors' experiments have shown that Pd and Pt porphyrin-based Gen 2 arylglycine dendrimers (AG2), modified at the periphery with 1-hexadecylamine possess high (ca millimolar) solubility in a variety of organic solvents (e.g., oils, saturated hydrocarbons, aromatic mineral oils, benzene, toluene, hexane, octane, tetrahydrofurane, saturated, alkanes, mineral oil, cooking oils, oils used in food or cosmetics, and organic liquids used in tissue and biological analyses, and any equivalent thereof), permitting phosphorescence measurements throughout the entire ambient oxygen range: $pO_2=0-160$ mm Hg.

The disclosure of each patent, patent application and publication cited or described in this document is hereby incorporated herein by reference, in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What we claim is:

1. A phosphorescent metalloporphyrin probe, also referred to as a dendritic oxygen probe, effective for oxygen measurement in human or animal tissue, said dendritic oxygen probe comprising a meso-unsubstituted, metallo-tetrabenzoporphyrin core, wherein the metal is Pd, and the Pd metallo-tetrabenzoporphyrin core has the following structure:

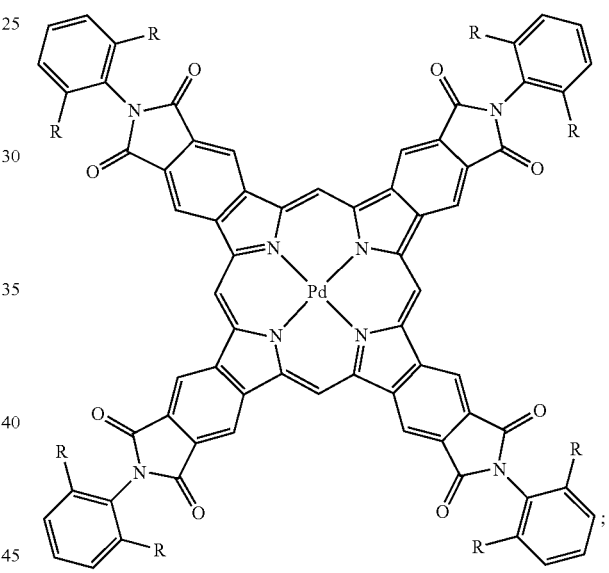

a dendrimer comprising dendrons, wherein the dendrons are peripherally attached to the metallo-tetrabenzoporphyrin core at the 2,6 positions indicated by "R"; and a solubilizing layer attached to the periphery of the dendrons.

2. The phosphorescent probe of claim 1, wherein the solubilizing layer is a polyethyleneglycol (PEG) layer.

3. The phosphorescent probe of claim 1, wherein the solubilizing layer is a hydrocarbon layer.

4. A method of making the probe of claim 1, comprising:

attaching flexible linkers terminated by functional groups to functional groups positioned directly on a meso-unsubstituted, metallo-tetrabenzoporphyrin core, wherein the metal is Pd, and the Pd metallo-tetrabenzoporphyrin core has the following structure:

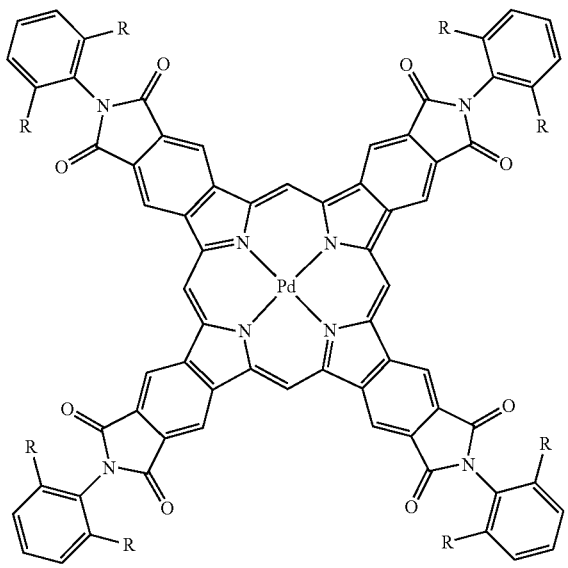

wherein "R" indicates the attachment of dendrons to the core at 2, 6 positions;
attaching dendrons to the functional groups of the linkers;
attaching solubilizing residues to peripheral functional groups on the dendrons to form a solubilizing layer.

5. A method of using a Pd-metalloporphyrin probe of claim 1, the method comprising the steps of:
dissolving the probe in the blood, and
exciting the probe using appropriate illumination, wherein the probe exhibits strong light absorption in a near infrared region of a spectrum and upon excitation, provides quantum yields of phosphorescence 5-10 fold higher, as compared with a corresponding tetraarylporphyrin when measured at the same temperature and conditions.

6. A method of improving dendrimerization of a meso-unsubstituted, metallo-tetrabenzoporphyrin core, wherein the metal is Pd, and the Pd metallo-tetrabenzoporphyrin core has the following structure

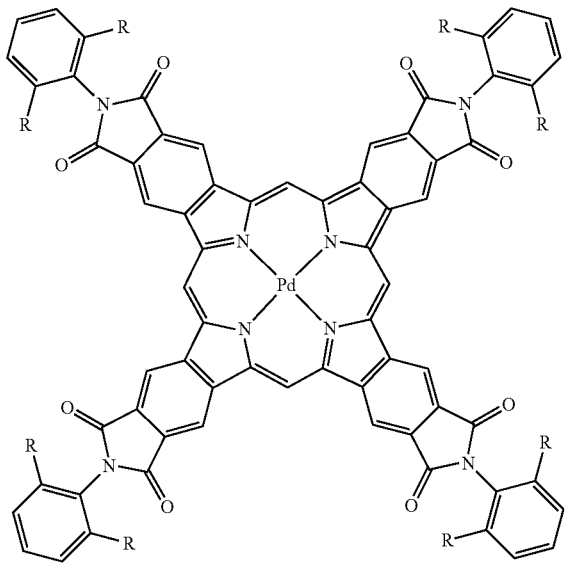

wherein "R" indicates the attachment of dendrons to the core at 2, 6 positions, the method comprising the steps of:
attaching flexible extension linkers terminated by functional groups to functional groups positioned directly on the metallo-tetrabenzoporphyrin core, and
thereby spacing reaction sites at a sufficient distance apart to cause enhancing of nucleophilic attack and reduce contamination by imperfect dendrimers in a yield and purity enhancing step.

7. A method of using the improved dendrimerization method of claim 6 using a Pd-metalloporphyrin probe, wherein the attachment of the flexible extension linkers provides 1-2 times higher-yield of synthesis of pure monodisperse dendritic oxygen probes as compared to corresponding phosphorescent porphyrins synthesized by the same steps of hydrolysis of peripheral ester groups, attachment of dendrons and hydrolysis of their peripheral esters and PEGylation, but without attaching flexible extension linkers to anchor groups during synthesis at the same temperature and conditions.

8. A phosphorescent metalloporphyrin probe having improved dendrimerization, also referred to as a dendritic oxygen probe, effective for oxygen measurement in human or animal tissue, said dendritic oxygen probe produced by the method of claim 6, the probe comprising added flexible extension linkers attached to anchor groups on either meso-aryl rings or directly on a metalloporphyrin macrocycle, thereby spacing reaction sites at a sufficient distance apart to enhance nucleophilic attack and reduce contamination by imperfectly reacted dendrimers after a reaction time of only the overnight period at room temperature.

9. A method of causing a dendritic phosphorescent probe suitable for oxygen measurements in aqueous liquids, the method comprising: adding a three dimensional supramolecular hydrophilic outer layer to the termini of a dendrimer having a meso-unsubstituted, metallo-tetrabenzoporphyrin core, wherein the metal is Pd, and the Pd metallo-tetrabenzoporphyrin core has the following structure:

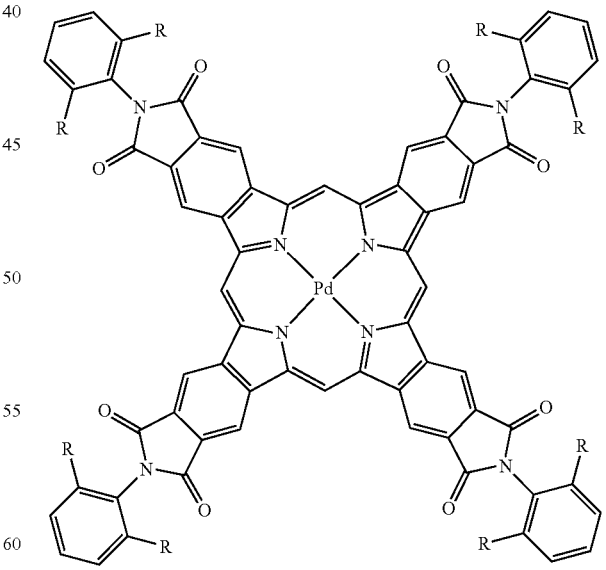

wherein "R" indicates the attachment of dendrons to the core at 2, 6 positions.

10. A method of causing a dendritic phosphorescent probe suitable for oxygen measurements in organic liquids, the method comprising:

adding a three dimensional supramolecular hydrophobic outer layer to the termini of hydrophobic dendrimers having a meso-unsubstituted, metallo-tetrabenzoporphyrin core, wherein the metal is Pd, and the Pd metallo-tetrabenzoporphyrin core has the following structure:

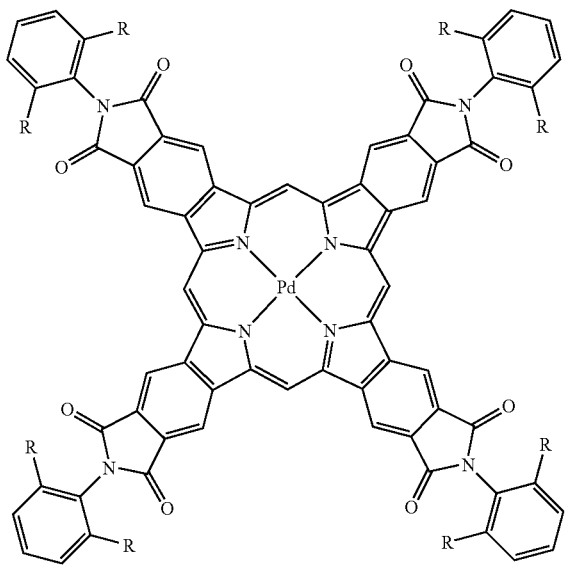

wherein "R" indicates the attachment of dendrons to the core at 2, 6 positions;

causing the molecule to remain folded, but to become highly soluble in organic solvents selected from the group comprising oils, saturated hydrocarbons, mineral oil and aromatic mineral oils, benzene, saturated alkanes, tetrahydrofuran (THF), toluene, hexane, octane, cooking oils, oils used in food or cosmetics, and organic liquids used in tissue and biological analyses; and enabling oxygen measurements therein.

11. A dendritic phosphorescent probe produced by the method of claim 10, comprising a selectably added three dimensional supramolecular hydrophobic outer layer attached to the termini of the hydrophobic dendrimers, thereby causing the molecule to remain folded, and to be highly soluble in organic solvents selected from the group comprising oils, saturated hydrocarbons, mineral oil and aromatic mineral oils, benzene, saturated alkanes, tetrahydrofuran (THF), toluene, hexane, octane, cooking oils, oils used in food or cosmetics, and organic liquids used in tissue and biological analyses.

* * * * *